United States Patent [19]

Laguna Granja et al.

[11] Patent Number: 5,856,316
[45] Date of Patent: *Jan. 5, 1999

[54] MIXTURE OF HIGHER PRIMARY ALIPHATIC ALCOHOLS, ITS OBTENTION FROM SUGAR CANE WAX AND ITS PHARMACEUTICAL USES

[75] Inventors: Abilio Laguna Granja; Juan Magraner Hernandez; Daisy Carbajal Quintana; Lourdes Arruzazabala Valmana; Rosa Mas Ferreiro; Milagros Garcia Mesa, all of Havana, Cuba

[73] Assignee: Laboratorios Dalmer SA, La Habana, Cuba

[ * ] Notice: The term of this patent shall not extend beyond the expiration date of Pat. No. 5,663,156.

[21] Appl. No.: 771,970

[22] Filed: Dec. 23, 1996

Related U.S. Application Data

[63] Continuation of Ser. No. 211,501, Jul. 25, 1994, which is a continuation of PCT/EP93/00007, Feb. 25, 1993.

[30] Foreign Application Priority Data

Sep. 29, 1992 [CU] Cuba .......................................... 107/92

[51] Int. Cl.$^6$ ........................... A61K 31/045; C07C 29/74

[52] U.S. Cl. ........................... 514/164; 568/840; 568/877; 568/920; 568/923

[58] Field of Search ..................................... 514/164, 724; 568/840, 877, 920, 921, 923

[56] References Cited

U.S. PATENT DOCUMENTS

| | | | |
|---|---|---|---|
| 2,021,926 | 11/1935 | Sexton et al. | 568/877 |
| 2,719,858 | 10/1955 | Hill | 552/545 |
| 5,166,219 | 11/1992 | Katz | 514/724 |
| 5,663,156 | 9/1997 | Granja et al. | 514/164 |

*Primary Examiner*—Alan L. Rotman
*Assistant Examiner*—Charanjit S. Aulakh
*Attorney, Agent, or Firm*—Lorusso & Loud

[57] ABSTRACT

A mixture of higher primary aliphatic alcohols of 22 to 38 carbon atoms can be obtained by saponifying and extracting steps with organic solvents from sugar cane wax. The mixture which contains tetracosanol, hexacosanol, heptacosanol, octacosanol, nonacosanol, triacontanol, dotriacontanol and tetratriacontanol can be used for the treatment of hypercholesterolemia, and atherosclerotic complications as platelet hyperaggregabiulity, ischemia and thrombosis, and prevents drug induced gastric ulcer and improves male sexual activity.

52 Claims, 19 Drawing Sheets

MIXTURE OF HIGHER PRIMARY ALIPHATIC ALCOHOLS, ITS OBTENTION FROM SUGAR CANE WAX AND ITS PHARMACEUTICAL USES

CROSS REFERENCE TO RELATED APPLICATION

This application is a continuation of copending U.S. patent application Ser. No. 08/211,501, filed Jul. 25, 1994, which is continuation of PCT/EP 93/00007 filed Feb. 25, 1993.

This invention is related to a mixture of higher primary aliphatic alcohols, containing alcohols of a range from 22 to 38 carbon atoms, especially those ranging from 24 to 34 carbon atoms and more especially, those with straight chain of 24, 26, 27, 28, 29, 30, 32 and 34 carbon atoms.

This mixture shows a relative composition of each alcohol, that is highly reproducible batch to batch.

According to the invention, the mixture of higher primary aliphatic alcohols (thereinafter called M.H.P.A.A.) obtained has specific pharmacological properties, hence it can be used as an active component in pharmaceutical formulations used as cholesterol-lowering, antiplatelet, anti-thrombotic and/or anti-isquemic agents, as well as for the antagonism of drug-induced ulcer and the improvement of male sexual activity.

Sugar cane wax and its natural source, mud, have always been a matter of interest, not only because of their industrial application, but also because of their chemical composition. The amount of wax in sugar cane ranges between 0.1% to 0.3%, depending on its variety.

During the agroindustrial process, only 40% of the wax content is diluted in the juice, the remaining material is lost in the bagasse.

From this 40%, 95% of it, are absorbed by the mud, from which raw wax is obtained. This wax is made up of esters, aldehydes, ketones, hydrocarbons, fatty acids and free alcohols, the amount of each depending on the variety and origin of the sugar cane plant and the technology used to obtain the wax.

The straight chain aliphatic alcohols obtained from sugar cane byproducts have been studied by several authors to learn about their composition and main features. The obtention of different groups of compounds from all kinds of waxes has been reported (J. A. Lamberton et al., 1959; Australian Journal of Chemistry 13, 261–268 and Horn A. and Martic J. S., 1957; Journal of Science Food and Agriculture 10, 571) who suggest a method for obtaining fatty alcohols from sugar cane cuticular wax based on the homogeneous saponification with alcoholic potassium hydroxide, following by the esterification of the unsaponifiable material and further molecular distillation.

It is also reported another method to isolate the alcohol mixture through a high efficiency high vacuum column. The high vacuum wax distilation for the chemical isolation of carbonylic compounds and the extraction of the remaining wax, using petrol ether. The solvent evaporates and the remaining content is acetylated for its further isolation through alumina chromatography. Finally, through alkaline hydrolysis alcohols are obtained and then recrystallized in ethanol, showing a fusion point ranging from 80° to 82° C.

A procedure for obtaining the mixture of higher aliphatic primary alcohols from animal and vegetable wax, is based on the saponification of the fatty esters followed by the extraction of alcohol mixtures through a fluid in sub- and supercritical state of $CO_2$, pressures ranging from 60–300 kg/cm$^2$ and temperatures between 25°–100° C. using adequate solvents, showing that depending on the solubility and at low temperature and pressure changes, selective extraction can be carried out. According to this procedure applied to the sugar cane wax, it is possible to obtain 5% of $C_{20}$ to $C_{36}$ alcohol mixtures.

Other project (Inada S., Furukawa K., Masui T., Honda K., Ogasawara J. and Tsubikamoto G.; 1986; Process for recovering primary normal aliphatic higher alcohols JP 60-119514) proposed a very similar extraction method applied to waxes, that is based on fluids in sub- and supercritical states of $CO_2$ with ethylene. The separation of organic compounds from their mixtures by means of fluids in sub- and supercritical states is also described. From the analytical point of view, all these are valuable methods, but high scale implementation is hindered by the use of column chromatography and molecular distillation, which are all not economic procedures.

One of the object of the invention is to obtain, isolate and purify the mixture of higher primary aliphatic alcohols (M.H.P.A.A.) of 24 to 34 carbon atoms from sugar cane wax, both from raw and refined wax.

The procedure of the present invention is based on a homogeneous phase saponification process of the sugar cane wax previously melted with concentrated solutions of alkaline and alkaline terrum hydroxides, especially with that of low molecular weight and more especially with that of sodium, potassium and calcium.

The concentration of the hydroxide solutions must be such that the ratio in weight of the corresponding hydroxide with that of the wax to be processed must be over 5% on, especially from 8 to 25%, and more especially from 15 to 25%. The saponification process lasts for a period of more than 30 minutes, especially from 2 to 5 hours. The solid obtained in this step is taken to a solid-liquid extractor, where M.H.P.A.A. is selectively extracted with adequate organic solvents, choosen among ketones from 3 to 8 carbon atoms, alcohols from 1 to 5 carbon atoms, hydrocarbons from 6 to 9 carbon atoms, haloforms as well as aromatic compounds such as benzene and its derivatives including mixtures of them. Some preferred solvents used in the present invention are the following: acetone, methyl ethyl ketone, pentanone, hexanone, heptanone, 2-methyl pentanone, ethanol, methanol, 2-propanol, butanol, terbutanol, pentane, hexane, heptane, octane, chloroform, 1,2-dichloroethane, dichloromethane, trichloroethane, 1,2,3-trichloropropane, benzene, toluene, phenol, p-methyl toluene and others.

The extraction is carried out in periods ranging between 5 to 10 hours. Afterwards, the product is successively crystallized using the above mentioned solvents or their mixtures. The yield attained ranges from about 30%, while the purity of M.H.P.A.A. attained ranges from 80 to 98% and more especially from 90 to 98%. M.H.P.A.A. thus obtained is formed by alcohols ranging from 22 to 38 carbon atoms. This is an off-white color mixture with a fusion point between 76.5° and 84.5° C. For the analysis of M.H.P.A.A. through gas chromatography in fused silica capillary column, these are derivatized by means of N-methyl-N-TMS-trifluoroacetamide (MSTFA).

The proposed procedure for obtaining M.H.P.A.A. from sugar cane wax has some advantages with regards to other previously reported. One of these advantages is related with the short process time. Another advantage of this invention is related with the high yields (near 30% in weight) that can be obtained by this process compared with the results previously described of Sho et al., which reports yields lower than 5%. Still another advantage of the proposed procedure is related with the purity degree of M.H.P.A.A. that can be obtained (near 98%) which are significantly higher than that reported by the state of the art. Thus, the method that has been proposed in the present invention is simpler and more appropiate for large scale production compared with that reported by Inada et al. (JP 60-119514) and also by Hagiwara Y. (JP 62-87537).

Table 1 shows the qualitative and quantitative composition composition of the mixture of M.H.P.A.A. obtained from sugar cane wax according to the invention.

TABLE 1

Qualitative and quantitative range of a composition of the M.H.P.A.A. used in phamaceutical formulations.

| Components | Proportion in the mixture |
| --- | --- |
| 1 - tetracosanol | 0.5–5.0% |
| 1 - hexacosanol | 5.0–15.0% |
| 1 - heptacosanol | 0.5–5.0% |
| 1 - octacosanol | 50.0–80.0% |
| 1 - nonacosanol | 0.5–3.0% |
| 1 - triacontanol | 6.0–20.0% |
| 1 - dotriacontanol | 1.0–10.0% |
| 1 - tetratriacontanol | 0.0–2.5% |

Table 2 shows a preferred composition of M.H.P.A.A. and Table 3 shows the most preferred composition of M.H.P.A.A. isolated from sugar cane wax.

TABLE 2

Preferred qualitative and quantitative range of a composition of M.H.P.A.A. used in pharmaceutical formulations.

| Components | Proportion in the mixture |
| --- | --- |
| 1 - tetracosanol | 0.5–1.0% |
| 1 - hexacosanol | 6.0–8.0% |
| 1 - heptacosanol | 2.5–3.5% |
| 1 - octacosanol | 60.0–70.0% |
| 1 - nonacosanol | 0.5–1.0% |
| 1 - triacontanol | 10.0–15.0% |
| 1 - dotriacontanol | 4.5–6.0% |
| 1 - tetratriacontanol | 0.5–2.0% |

TABLE 3

Most preferred qualitative and quantitative range of a composition of M.H.P.A.A used in pharmaceutical formulations.

| Components | Proportion in the mixture |
| --- | --- |
| 1 - tetracosanol | 0.8 +/- 0.1% |
| 1 - hexacosanol | 6.7 +/- 0.3% |
| 1 - heptacosanol | 3.0 +/- 0.3% |
| 1 - octacosanol | 65.6 +/- 3.4% |
| 1 - nonacosanol | 0.7 +/- 0.1% |
| 1 - triacontanol | 12.5 +/- 0.6% |
| 1 - dotriacontanol | 5.0 +/- 0.4% |
| 1 - tetratriacontanol | 0.8 +/- 0.1% |

M.H.P.A.A. resp its pharmaceutical formulations may be administered to human and animal beings. The daily dosage of M.H.P.A.A. varies considerably depending on the treatment of the different diseases and the actual state of the living being, but may usually be established between 1 to 100 mg per day, preferably about 3–20 mg. M.H.P.A.A. may e.g. be administerd orally or parenterally. A preferred route are orally administered film-coated tablets as well as granules or capsules.

Pharmaceutical formulations contain as an active ingredient from 0.5 to 15.0% wt of M.H.P.A.A. This dosage is obtained by mixing M.H.P.A.A. with different excipients such as agglutinants, disintegrators, lubricants, sliders or just fillers. In these excipients are included lactose, corn starch, saccharose, magnesium stearate, microcrystalline cellulose, sodium croscarmellose gelatin, cellulose acetophtalate, titanium dioxide, special talc for tablets and polyethylenglycol.

Lipid-lowering effects of sugar cane wax have been demonstrated in rats (Fukuda, Effects of sugar cane wax on serum liver lipids on rats; Chemical Abstracts, 106, 17, 137413p) and also by Sho H. et al. (1984; Effects of Okinawan sugar cane wax and fatty alcohols on serum and liver lipids in the rats; J. Nutri. Vitaminol. 30,6,553–559).

Firstly, effects of sugar cane wax on serum and liver lipids were investigated in male Wistar rats fed high levels of plants and animal fats. The authors found that addtion of 0.5% of sugar cane wax to dietary fat reduces significantly serum triglycerides in rats fed plant or animal fats, but only in the last ones cholesterol levels decreased significantly, without affecting the content of liver lipids. Hence, authors concluded that sugar cane wax shows hypolipidemic effects.

On the other hand, Sho H. et al. (1984) studied the effects of Okinawan sugar cane wax on serum and liver lipids in rats fed a diet containing 0.5% of this wax and they found a significant reduction of both serum and liver cholesterol content. Nevertheless, no significant variation in cholesterol levels were found when were used fatty alcohols from the same wax in the diet of animals. Thus, they discarded that lipid-lowering properties of the wax were attributable to these alcohols.

However, some years later, Shimura S., Hagesawa T., Takano S. and Susuki T. (1987: Studies on the effect of octacosanol on the motor endurance in mice; Nutrition Reports Int. 36, 1029–1038) studied the effects of octacosanol in mice subjected to physical activity and fed octacosanol-enriched diet. They found that octacosanol isolated from sugar cane wax significantly reduces the content of both triglycerides and cholesterol in the liver, while only serum levels of triglycerides were reduced in a significant manner. They concluded that octacosanol isolated from sugar cane wax showed lipid-lowering properties, which disagrees with the previous results of Sho H. et al. (1984) aforementioned.

Likewise, antilipaemic effects have been also further attributed to hexacosanol, another higher primary aliphatic alcohol, although very high doses were reported as needed to obtain such results (10–30 mg/kg/day) (Hagiwara Y. 1987: Antilipaemic agents containing hexacosanol used to treat hypertension, arteriosclerosis, diabetes mellitus, heart disease and obesity; JP A 62 099323).

There are different commercial lipid-lowering drugs considered as effective, safe and well tolerated, but most of them produce different adverse side effects. Since lipid-lowering therapy must be aministered chronically, this aspect is very important.

For example, gemfibrozil reduces serum triglycerides, raises HDL-C levels and produces a mild decrease of serum cholesterol, but several adverse effects have been reported. Thus, gastrointestinal effects, such as epigastric pain, diarrhoea, nausea, vomiting and flatulence have been referred. Moreover, headache, dizziness, blurred vision, impotence, decreased libido and liver function abnormalities such as increased transaminases, LDH, creatinphosphokinase and alkaline phosphatase have occurred in gemfibrozil-treated patients. Likewise, it should not be administered to patients with renal failures.

Probucol is another lipid-lowering drug with antioxidant properties that causes mild decreases of serum cholesterol and LDL-C. Nevertheless, a disadvantage of its lipid-lowering action is that it reduces the HDL-C fraction. Moreover, several adverse effects as gastrointestinal disturbances in approximately 10% of the population, as well as a considerable variation in the electrocardiogram have been reported.

Other lipid-lowering drugs used frequently are Cholestiramine and Cholestipol. These are effective first-line cholesterol-lowering drugs that strongly decrease serum cholesterol and LDL-C, but tend to increase triglyceride levels. These drugs induced several gastrointestinal symptoms, mainly constipation. Compliance with the treatment is generally low, because the adverse symptoms and since they are not easy-to-take agents, requiring doses up to 12 to 20 g/day to achieve the desired effects. Moreover, adverse chemical interactions with other drugs such as digitoxin have been described.

Lovastatin is the first of the "statins", drugs acting as. inhibitors of HMGCoA-reductase and thus efficiently reducing serum cholesterol and LDL-C levels, it also moderately increases HDL-C and decreases triglycerides. Several adverse effects have been reported for this drug. Thus, the main adverse effects are miopathy, mild to moderate increases of creatinphosphokinase and persistent increases in serum transaminases, that frequently became reversible after withdrawal of the treatment. Miopathy has occurred mainly in patients receiving concomitant therapy with inmunosuppresive drugs as gemfibrozil or niacin. Moreover, adverse effects such as skin rash, pruritus, headache and severe muscular lesions in sensitive patients resulting in myolisis have also been reported by lovastatin-treated patients. Moreover, drug-related occurrence of testicular atrophy and hepatic tumors in laboratory animals has been reported.

Similar, simvastatin and pravastatin are other "statins", acting by the same mechanism of lovastatin and showing approximately the same cholesterol-lowering effects. Adverse effects reported by these patients are similar to those reported for lovastatin-treated patients, but claimed as slightly lower. Simvastatin and pravastatin-treated patients reported constipation, flatulence, nausea, headache, fatigue, subcutaneous rash and myopathies affecting creatin phosphokinase.

On the other hand, it has been described that treatment with some lipid-lowering drugs reduces the tendency to platelet hyperaggregation frequently seen in hyperlipidemic patients and experimental data have shown anti-aggregatory effects mediated by these compounds. Nevertheless, only some cholesterol-lowering drugs show this property. As has been referred, atherosclerosis is a variable combination of changes of the intima of the arteries consisting of the focal accumulation of lipids, complex carbohydrates, blood and blood products, fibrous tissue and calcium deposits, frequently also associated with medial changes. Thus, this definition indicates atherosclerosis as a multifactorial process, not only including hyperlipidaemia as risk factor.

Thus, between factors contributing to atherosclerosis development platelet aggregation has a very important place. Platelet releasing granule contents activating arachidonic acid, which metabolizes into cyclic endoperoxides. These are mainly transformed into cyclic endoperoxides and finally rendering thromboxane $A_2$ ($TxA_2$), a strong vascular vasoconstrictor and platelet aggregatory agent. Platelet aggregation can be elicited by different compounds, such as collagen, ADP and epinephrine, between others. Thus, different experimental "in vivo", "ex vivo" or "in vitro" models testing effectiveness of putative antiplatelet drugs commonly explored their effect on platelet aggregation induced by these agents.

These tests are also used for testing platelet aggregation in healthy volunteers and in patients with diseases frequently inducing hyperaggregability, such as hypercholesterolemia and diabetes, between others. Between these tests, collagen-induced platelet aggregation is one of the most frequently used. Thus, as example, collagen injected endovenously leads to reversible intravascular platelet aggregation "in vivo" and aggregates of platelets enter to the vascular microcirculation, subsequently decreasing the count of circulating platelet and simultaneously increasing the plasma MDA concentration. Moreover, in some species this injection of collagen induces mortality produced by thrombosis. In these models, antiplatelet drugs generally prevent the decrease of platelet content and increase of MDA concentration, as well as the collagen induced mortality.

Some drugs showing platelet anti-aggregatory effects are useful for treatment of thrombotic diseases, myocardial infarction and stroke, but not all of them show these advantages. On the other hand, there are antithrombotic drugs that mainly acting by lytic processes affecting blood coagulation, but not on the platelet aggregation such as streptokinase and urokinase.

Since ischemic cardiovascular diseases, stroke and vascular peripheric obstructive pathologies are the main sequel of atherosclerosis, effects of several drugs on these complications are commonly tested. Thus, theoretically a drug showing cholesterol-lowering properties that also can prevent these complications by acting on other events involved in these processes must be advantageous for treating these patients. Likewise, reduction of $TxA_2$ levels have been associated not only with antiplatelet and antithrombotic effects, but also with antiischemic effects. The pharmacological screening of antiischemic drugs commonly includes the evaluation of their effects on brain-induced global ischemia. Thus, it has been described the protective effect of different drugs on rat cerebral ischemia for certain nonsteroidal anti-inflammatory drugs (NSAID) which inhibits reactions catalyzed by cicloxygenase, as well as specific inhibitors of thromboxane synthetase and prostacyclin analogues ($PgI_2$) (Borzeix M. G. and Cahn J.; 1988; Effects of new chemically metabolically stable prostacyclin analogues on early consequences of a transient cerebral oligemia in rats; Prostaglandins 35, 5, 653–664).

Other experimental models, such as global ischemia induced experimentally in Mongolian gerbils are also used frequently.

Acetylsalicylic acid (ASA) is a compound exhibiting antiplatelet, antithrombotic and anti-ischemic properties in experimental models and human beings. It is the drug most widely used for treatment of acute myocardial infarction and stroke, as well as for preventing thromboembolic disorders. ASA effects are supported by its well known inhibition of cyclooxygenase, a key enzyme on the arachidonic acid metabolism. Thus, ASA induces a significant and remarkable reduction of serum levels of thromboxane $A_2$ ($TxA_2$) a recognized patophysiological agent for the vascular endothelium and it explains the aforementionend effects of ASA.

Nevertheless, since the ASA inhibition is exerted at cyclooxygenase level, not only TxA$_2$ levels are reduced, but also levels of prostacyclin (PgI$_2$) a compound with pharmacological properties opposite of that showed by TxB$_2$. On the other hand, taking into account that ASA inhibits the synthesis of prostaglandins (series E), it induces gastric damages because it prevents the cytoprotective effects of prostaglandins. This is the basis of the main adverse side effect reported for ASA, that is, gastritis, gastric ulcera and related disturbances.

An object of the invention is to place at the public's disposal M.H.P.A.A. of 24 to 34 carbon atoms for pharmaceutical formulations.

Another object of the invention is to use M.H.P.A.A. of 24 to 34 carbon atoms at relatively low doses as a active ingredient of pharmaceutical formulations used as cholesterol-lowering drug.

Still another object of the invention is the use of M.H.P.A.A. in pharmaceutical formulations used as antiplatelet, antiischemic or antithrombotic agents and to demonstrate the platelet antiaggregatory effects of M.H.P.A.A. which has been confirmed in different experimental series in "ex vivo" and "in vivo" models, as well as in human beings.

Still another object of the invention is to demonstrate the protective effect of M.H.P.A.A. on ischemia induced experimentally.

Still another object of the invention is to demonstrate that M.H.P.A.A. shows pharmacological interaction with ASA, the drug most commonly used for cerebral ischemic therapy. Thus, results showed a synergism between antiplatelet, anti-thrombotic and anti-ischemic properties of M.H.P.A.A. and ASA.

Still another object of the invention is to demonstrate that M.H.P.A.A. reduced significantly the gastric ulcera induced e.g. by aspirin, ethanol, indomethacine, compound C 4880 (Sigma) and other medications producing gastric ulcer in human beings under treatment. It has been described that gastric ulcer induced by alcohol is mainly related with an increase of TxA$_2$ as physiological agent, while ulcer induced by C 4880 mainly involves serotonergic mechanisms, although a role of TxA$_2$ in its ethiogenesis can not be ruled out. On the other hand, gastric ulcer induced by ASA is related with the inhibition of prostaglandins (E series) synthesis produced by ASA, since they have a cytoprotective effect on the gastric mucosa. It has been demonstrated that the TxA$_2$ to PgI$_2$ ratio in gastric mucosa plays an important role as an endogenous mechanism of its integrity.

On the other hand, as previously mentioned, some cholesterol-lowering drugs impair male sexual activity. Thus, decreased libido and impotence have been reported by patients treated with clofibrate and gemfibrozil.

At the contrary, another objective of this invention is to demonstrate that M.H.P.A.A. does not only not impair male sexual activity, but also increases sexual activity on animals and humans. Thus, there are a number of hypercholesterolemic patients who have reffered improvement of sexual activity during the treatment performed in the clinicals trials. This effect is not related with changes on the serum levels of testosterone, the main hormone regulating libido and sexual behavior.

Testosterone has been considered as the main sexual hormone regulating libido in mammals. It has been described that only threshold levels of testosterone are required for sexual activity and overthreshold levels do not induce further increases of male sexual behavior. Nevertheless, more recently it has been demonstrated that same levels of testosterone involving different patterns of hormone release or administration can induce different effects on male sexual activity. This indicates that this aspect still remain controversial.

On the other hand, male sexual behavior in mammals include different steps: libido, penile werection, orgasm and ejaculation that are controlled by complex neuroendocrine mechanisms. Thus, this behavior is determined by release of testicular hormones acting on peripheral effectors, elicited and feed-back mechanisms acting on the central nervous system mainly located in the mediobasal hypothalamic region. Both dopaminergic and serotonergic pathways control sexual activity.

Finally, it has been proved that nitric oxide (NO) release at corpora cavernosa is a crucial mechanism envolved in penile erection. Thus, the effect of M.H.P.A.A. improving male sexual behavior can be explained by alternative mechanisms not fully elucidated yet.

Finally, in a whole picture of M.H.P.A.A. profile, its very good safety and tolerability represent an important advantage compared with the drugs of the state of the art. Thus, results obtained in acute, subchronic and chronic studies conducted in rodents, rabbits, Beagle dogs and monkeys showed no drug-related toxicity. Moreover, it does not show any mutagenic effect nor has teratogenic effects in rabbits or rats. M.H.P.A.A. administration over two generations did not affect fetal developement nor reproductive performance in rats. Finally, a 24 months carcinogenecity study conducted in rats also showed the lack of toxicity and carcinogenic effects of M.H.P.A.A.

Short and long-term clinical trials also support the excelent safety and tolerability of the treatment.

The purpose of the invention shall be described in detail in the following examples. The examples shall not be limiting the scope of said invention.

EXAMPLE 1

1,000 g of refined wax from sugar cane are taken to be melted at 100°–110° C., adding 200 g of potassium hydroxide dissolved in 150 ml of water. This process is maintained for 5 hours with stirring. M.H.P.A.A. is extracted from the solid obtained in the process for 12 hours in a solid-liquid extraction system using heptane as solvent. The extract obtained is cooled at room temperature, whereby M.H.P.A.A. is crystallized and recrystallized in methyl ethyl ketone. As much as 285 g of this alcohol mixture were obtained with a purity amounting to 94.70%. The melting point of the mixture ranges between 80.5° and 82.5° C. Table 4 shows the qualitative and quantitative composition of M.H.P.A.A. obtained using this procedure.

TABLE 4

Qualitative and quantitative composition of M.H.P.A.A. obtained.

| Component | Percentage of each alcohol |
| --- | --- |
| 1 - tetracosanol | 0.81 |
| 1 - hexacosanol | 7.00 |
| 1 - heptacosanol | 2.81 |
| 1 - octacosanol | 65.09 |
| 1 - nonacosanol | 0.67 |
| 1 - triacontanol | 12.43 |
| 1 - dotriacontanol | 5.05 |
| 1 - tetratriacontanol | 0.84 |

EXAMPLE 2

Two (2) kg of raw wax from sugar cane are taken to be melted at 85°–100° C., to which 300 g of sodium hydroxide dissolved in 200 ml of water are added, the saponification process remains for a period of four hours with stirring. The extraction of M.H.P.A.A. is implemented using chloroform as solvent for a period of 10 hours in a conventional solid-liquid extraction system, whereby the extract obtained is cooled at room temperature, the solid obtained is recrystallized in methanol and finally in a chloroform/methyl ethyl ketone mixture. M.H.P.A.A. (405 g) was obtained with a purity amounting to 92.52%. M.H.P.A.A. melting point ranges from 79.0° and 80.5° C. Table 5 shows the qualitative and quantitative composition of M.H.P.A.A. obtained using this procedure.

TABLE 5

Qualitative and quantitative composition of M.H.P.A.A. obtained.

| Component | Percentage of each alcohol |
|---|---|
| 1 - tetracosanol | 0.87 |
| 1 - hexacosanol | 6.84 |
| 1 - heptacosanol | 3.08 |
| 1 - octacosanol | 62.92 |
| 1 - nonacosanol | 0.80 |
| 1 - triacontanol | 12.66 |
| 1 - dotriacontanol | 4.65 |
| 1 - tetratriacontanol | 0.70 |

EXAMPLE 3

Twelve kg of calcium hydroxide dissolved in 7 L of water are added to 50 kg of refined sugar cane wax—previously melted at 100°–120° C. The saponification process is continued for 7.5 hours with stirring. M.H.P.A.A. is extracted using ethanol as solvent for 12 hours in a solid-liquid extraction system. The obtained extract is left to cool at room temperature, later this solid is recrystallized in chloroform. M.H.P.A.A. (13.7 kg) is obtained with a purity of 93.77%. The melting point of the mixture ranges from 80.0°–82.0° C. Table 6 shows the qualitative and quantitative composition of M.H.P.A.A. obtained using this procedure.

TABLE 6

Qualitative and quantitative composition of M.H.P.A.A. obtained.

| Component | Percentage of each alcohol |
|---|---|
| 1 - tetracosanol | 0.71 |
| 1 - hexacosanol | 6.88 |
| 1 - heptacosanol | 3.06 |
| 1 - octacosanol | 64.70 |
| 1 - nonacosanol | 0.62 |
| 1 - triacontanol | 12.01 |
| 1 - dotriacontanol | 5.09 |
| 1 - tetratriacontanol | 0.70 |

EXAMPLE 4

8.6 kg of calcium hydroxide dissolved in 4.5 l of water are added to 50 kg of raw sugar cane wax, previously melted at 100°–120° C. The saponification process is done with continuous stirring for three hours. M.H.P.A.A. is extracted with dichloromethane as solvent for 12 hours in a solid-liquid extractor. The product obtained is left to cool at room temperature and the solid obtained is recrystallized in a mixture of hexane and acetone 1:1. The alcohols mixture (6.8 kg) was obtained with a purity of 92.91%. The melting point of M.H.P.A.A. is 78.5°–80.5° C. Table 7 shows the qualitative and quantitative composition of M.H.P.A.A. obtained by this procedure.

TABLE 7

Qualitative and quantitative composition of the M.H.P.A.A. obtained.

| Component | Percentage of each alcohol |
|---|---|
| 1 - tetracosanol | 0.75 |
| 1 - hexacosanol | 7.00 |
| 1 - heptacosanol | 3.14 |
| 1 - octacosanol | 63.60 |
| 1 - nonacosanol | 0.62 |
| 1 - triacontanol | 12.03 |
| 1 - dotriacontanol | 4.99 |
| 1 - tetratriacontanol | 0.78 |

EXAMPLE 5

Twenty (20) kg of refined sugar cane wax previously melted at a temperature of 100°–110° C., are taken, adding 3.7 kg of potassium hydroxide diluted in 3.0 L of water. The saponification process lasted 5 hours performed with continuous stirring. The extraction of M.H.P.A.A. is performed with a Soxhlet extractor using methyl ethyl ketone as solvent for 14 hours. The extracted material is cooled at room temperature. Further on, it is recrystallized into a mixture of hexane:chloroform 1:1. M.H.P.A.A. (3.8 kg) was obtained with a purity accounting for a 92.56%. The melting point of M.H.P.A.A. ranges between 78.5° and 80.5° C. Table 8 shows the qualitative and quantitative composition of M.H.P.A.A. obtained using this procedure.

TABLE 8

Qualitative and quantitative composition of M.H.P.A.A. obtained.

| Component | Percentage of each alcohol |
|---|---|
| 1 - tetracosanol | 0.85 |
| 1 - hexacosanol | 6.56 |
| 1 - heptacosanol | 3.10 |
| 1 - octacosanol | 63.10 |
| 1 - nonacosanol | 0.72 |
| 1 - triacontanol | 12.18 |
| 1 - dotriacontanol | 5.31 |
| 1 - tetratriacontanol | 0.74 |

EXAMPLE 6

One kg of raw sugar cane wax melted previously at 100° C., adding 250 g of calcium hydroxide. The saponification process is done with continuous stirring for 2 hours. M.H.P.A.A. is extracted using 2-propanol as solvent for 12 hours in a solid-liquid extraction system. The product obtained is cooled at room temperature, whereby is recrystallized using heptane. M.H.P.A.A. (165 g) was obtained with a purity of 93.63%. The melting point of this M.H.P.A.A. ranges from 80.0° to 81.5° C. Table 9 shows the qualitative and quantitative composition of M.H.P.A.A. obtained using this procedure.

TABLE 9

Qualitative and quantitative composition of M.H.P.A.A. obtained.

| Component | Percentage of each alcohol |
| --- | --- |
| 1 - tetracosanol | 0.84 |
| 1 - hexacosanol | 6.52 |
| 1 - heptacosanol | 3.18 |
| 1 - octacosanol | 64.13 |
| 1 - nonacosanol | 0.69 |
| 1 - triacontanol | 12.54 |
| 1 - dotriacontanol | 4.93 |
| 1 - tetratriacontanol | 0.80 |

EXAMPLE 7

Two (2) kg of refined sugar cane wax were melted previously at 110° C., adding 400 g of sodium hydroxide diluted in 200 ml of water. This process is mantained for 3 hours with continuous stirring. The extraction of M.H.P.A.A. is performed using toluene as solvent in a solid extractor for 6 hours, whereby it was secondly recrystallized using methanol as solvent. M.H.P.A.A. (389 g) was obtained with a purity accounting 95.10%. The melting point of the mixture ranges between 81.0° and 83.0° C. Table 10 shows the qualitative and quantitative composition of M.H.P.A.A. obtained using this procedure.

TABLE 10

Qualitative and quantitative composition of M.H.P.A.A. obtained.

| Component | Percentage of each alcohol |
| --- | --- |
| 1 - tetradosanol | 0.80 |
| 1 - hexacosanol | 7.00 |
| 1 - heptacosanol | 2.82 |
| 1 - octacosanol | 64.54 |
| 1 - nonacosanol | 0.72 |
| 1 - triacontanol | 13.02 |
| 1 - dotriacontanol | 5.31 |
| 1 - tetratriacontanol | 0.89 |

EXAMPLE 8

Five (5) kg of refined sugar cane wax were treated with 1 kg of potassium hydroxide diluted in 500 ml of water after melting it at 120° C. This process is mantained for 4 hours with continuous stirring. M.H.P.A.A. is extracted using ethanol as solvent, in a solid-liquid extraction system during 5 hours. After that, the extract is cooled at room temperature, whereby M.H.P.A.A. is crystallized using toluene as solvent. M.H.P.A.A. (1,490 g) was obtained with a purity accounting for a 92.20%. The melting point of M.H.P.A.A. ranges between 79.5° and 81.0° C. Table 11 shows the qualitative and quantitative composition of M.H.P.A.A. obtained using this procedure.

TABLE 11

Qualitative and quantitative composition of M.H.P.A.A. obtained.

| Component | Percentage of each alcohol |
| --- | --- |
| 1 - tetracosanol | 0.76 |
| 1 - hexacosanol | 6.58 |
| 1 - heptacosanol | 2.84 |
| 1 - octacosanol | 62.43 |
| 1 - nonacosanol | 0.71 |
| 1 - triacontanol | 13.08 |
| 1 - dotriacontanol | 5.05 |
| 1 - tetratriacontanol | 0.75 |

EXAMPLE 9

The compositions of two different developed pharmaceutical formulations, using M.H.P.A.A. as active principle, are shown in Table 12. These formulations were developed taking into account the physical, chemical and physico-chemical characteristics of the active principle.

The formulations were manufactured by a wet granulation process mixing the active principle and the pharmaceutical excipients with controlled portions, drying, degranulating, lubricating and stamping them.

TABLE 12

Pharmaceutical formulations using M.H.P.A.A. as active principle.

| Component | Formulation 1 | Formulation 2 (%) |
| --- | --- | --- |
| M.H.P.A.A. | 5.0 | 15.0 |
| Lactose | 56.0 | 54.0 |
| Com Starch | 15.0 | 10.0 |
| Gelatin | 2.5 | 2.0 |
| Sodium croscarmellose | 5.0 | 4.0 |
| Saccharose | 5.0 | 4.0 |
| Talc | 2.0 | 2.0 |
| Magnesium stearate | 1.5 | 1.0 |
| Cellulose acetophtalate | 0.5 | 1.0 |
| Microcrystalline cellulose | 7.5 | 7.0 |

EXAMPLE 10

Male New Zealand rabbits (2–3 kg) were adapted to laboratory conditions for 15 days and randomly distributed in 4 experimental groups: a control (only receiving vehicle) and 3 M.H.P.A.A. treated groups at 5, 50 and 200 mg/kg receiving M.H.P.A.A. suspended in an Acacia gum/water vehicle by gastric gavage (1 ml/kg) for 4 weeks. Lipid profile was determined at baseline (the day before starting the treatment and 4 weeks after). M.H.P.A.A. administered orally at 5, 50 and 200 mg/kg during 30 days significantly reduced (Wilcoxon $p<0.05$) in a dose-dependent manner total cholesterol and LDL-serum levels. Moreover, the percent changes in control and treated groups were statistically different (Mann Whitney U, *$p<0.05$), see FIGS. 1–4.

FIG. 1 shows the effect of M.H.P.A.A. on serum cholesterol levels, FIG. 2 on serum LDL-C levels, FIG. 3 on serum cholesterol changes and FIG. 4 on serum LDL-C changes (%) in normocholesterolemic rabbits.

In this experimental series, the highest dose of M.H.P.A.A. administered (200 mg/kg) reduced serum cholesterol and LDL-C by 51% and 78%, respectively.

Figure 1:
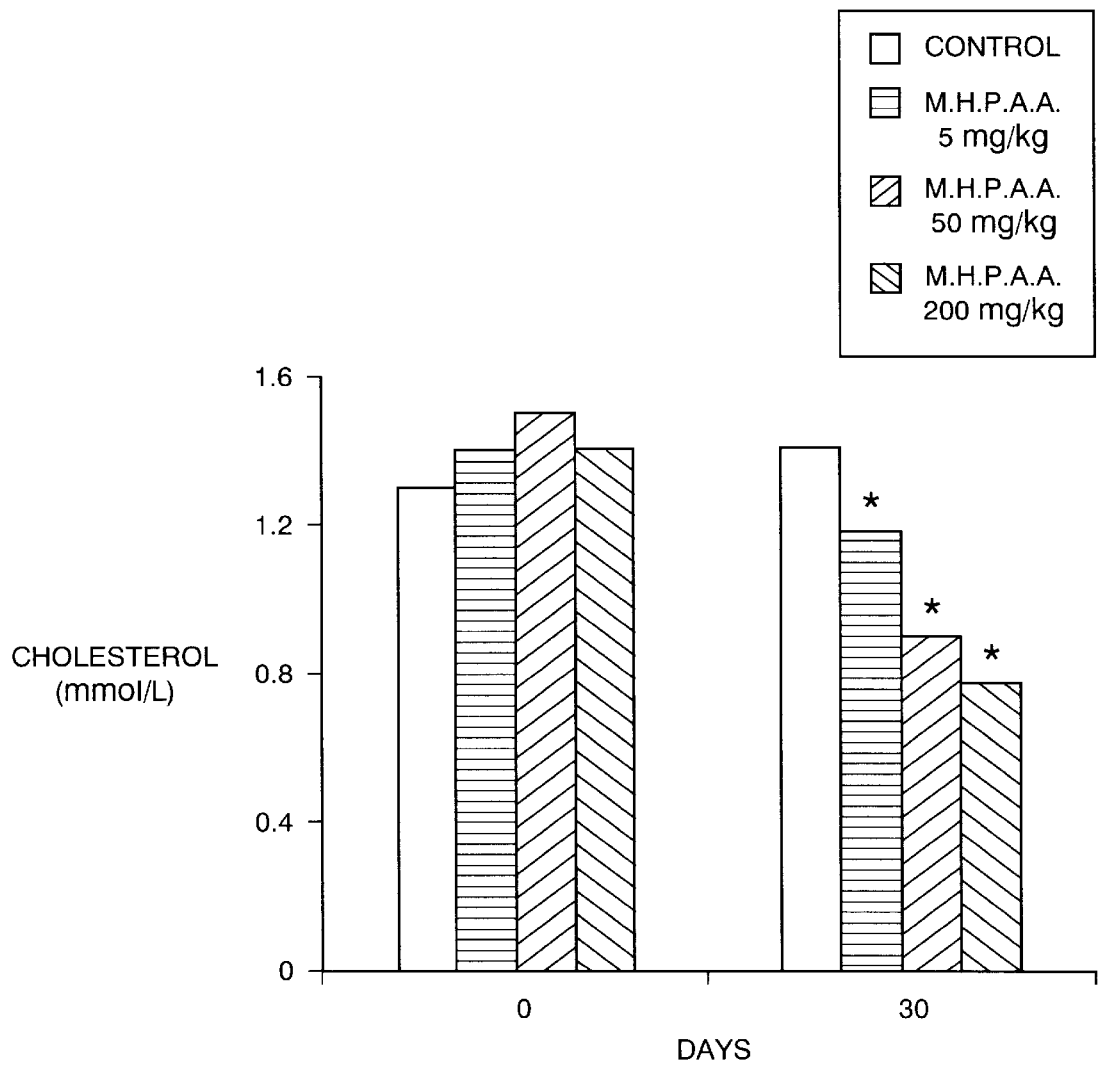
Figure 2:
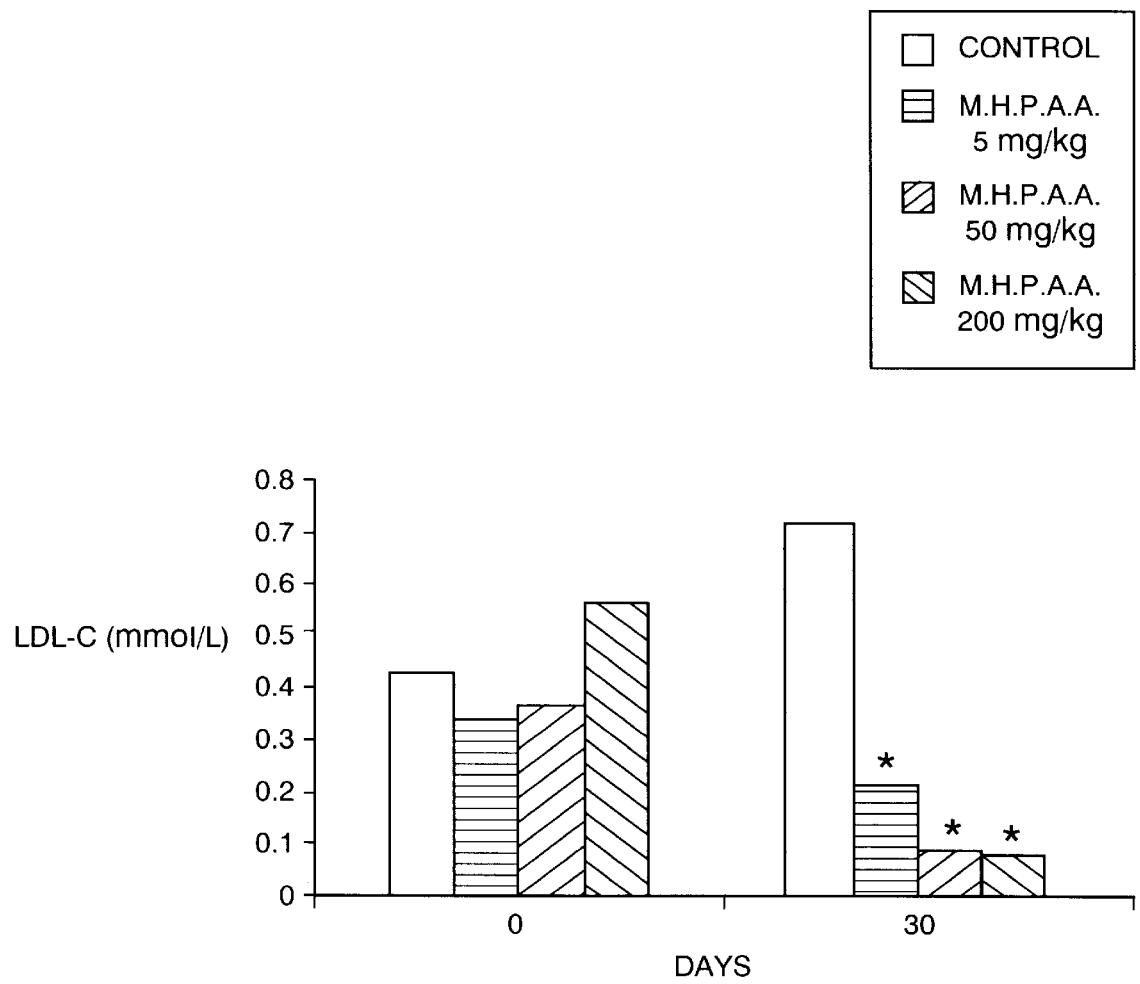
Figure 3:
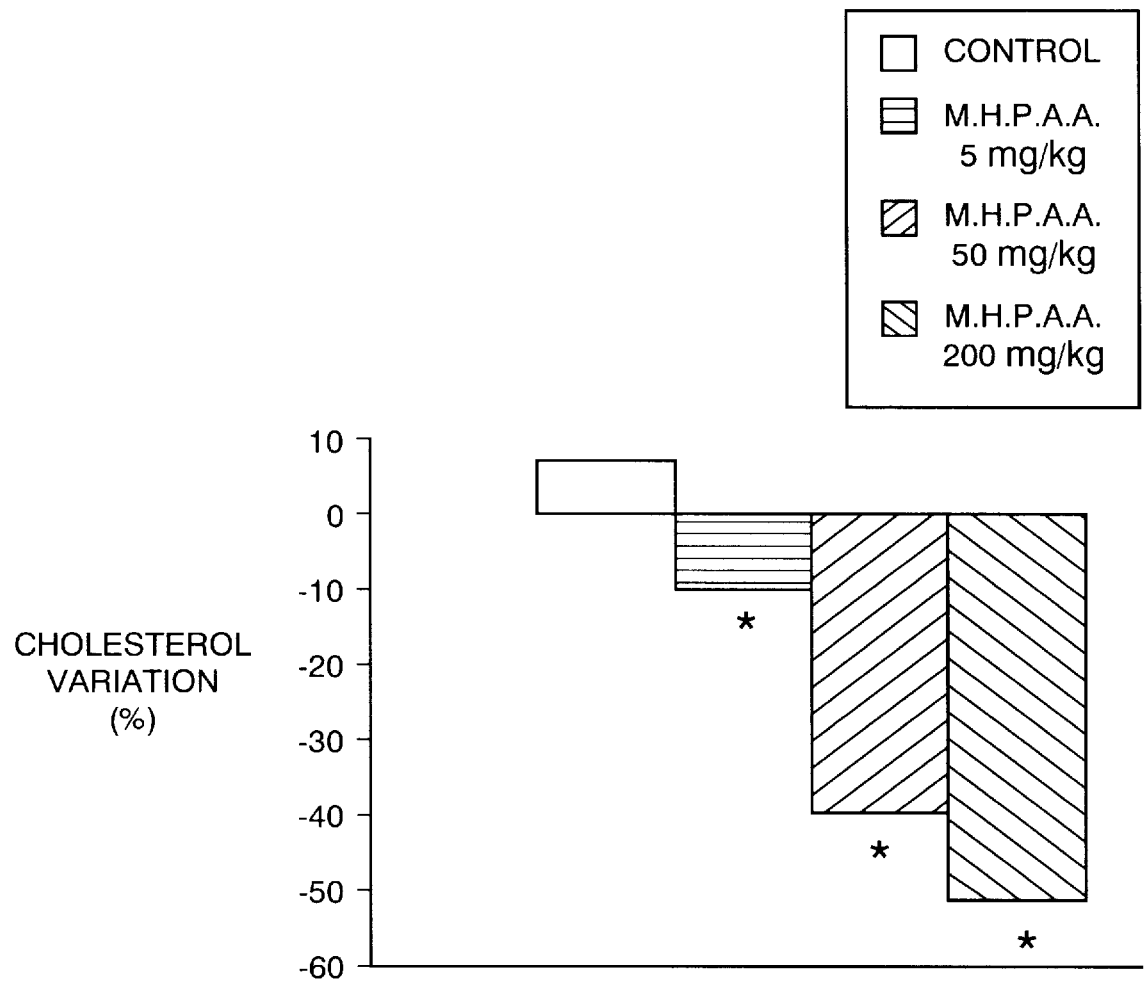
Figure 4:
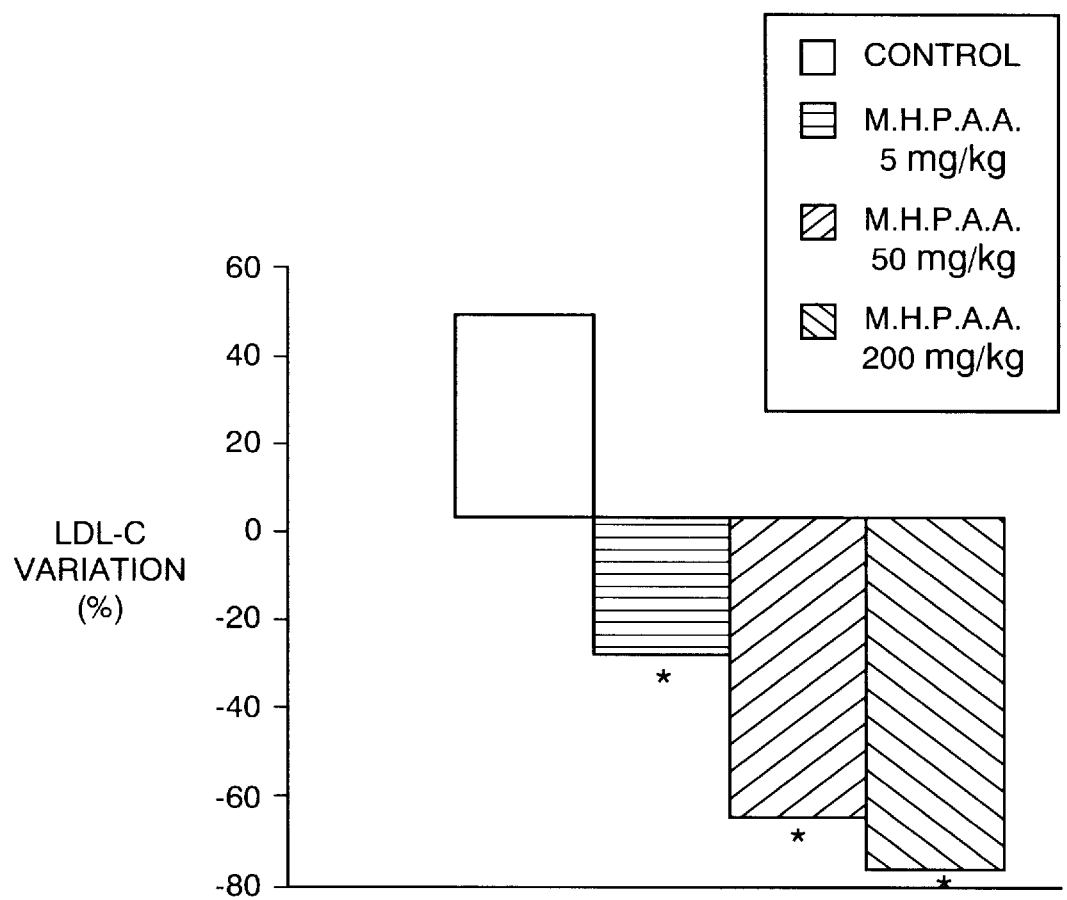
Figure 5:
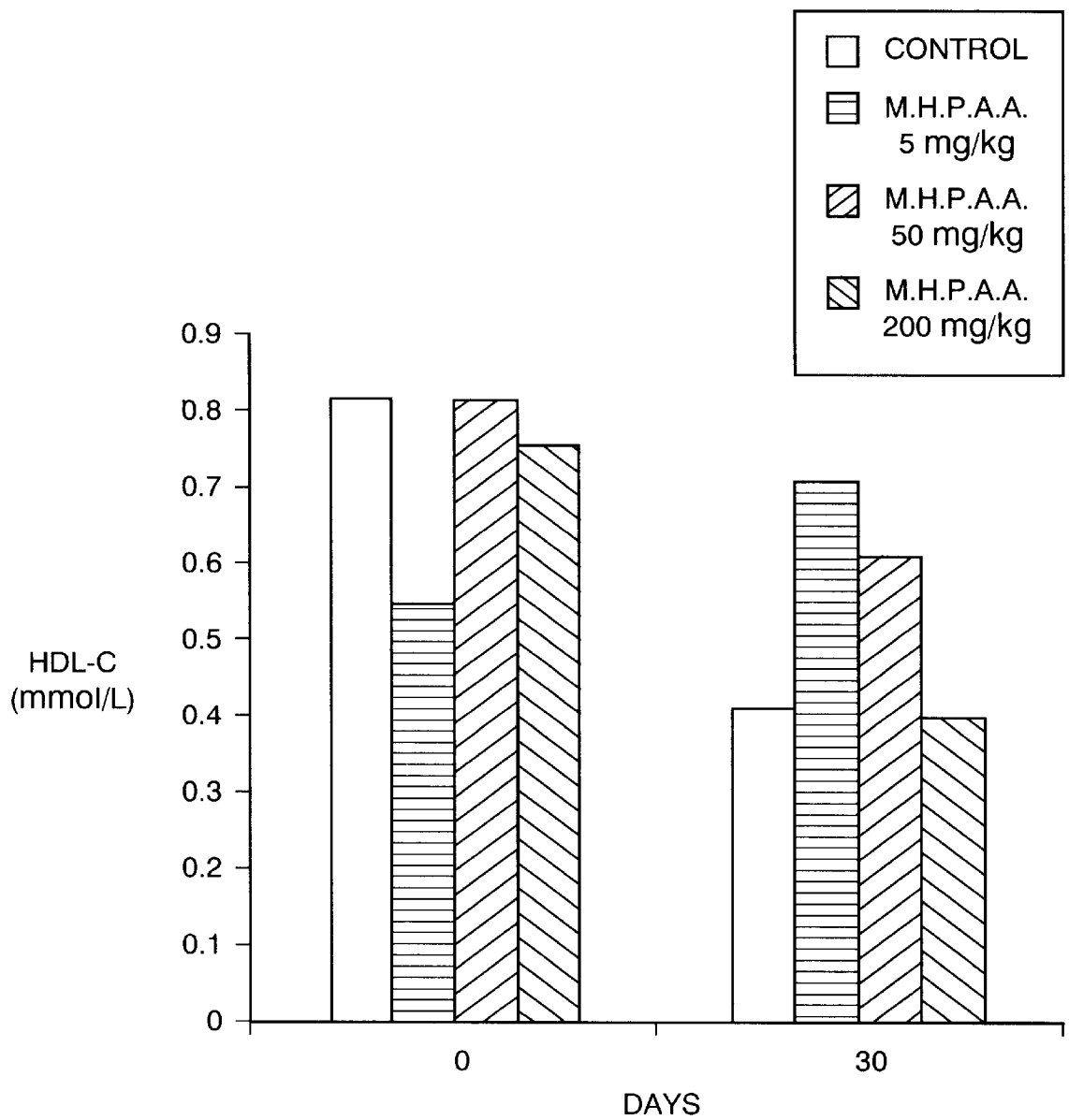
FIG. 5 shows the effect of M.H.P.A.A. on serum HDL-C levels in normocholesterolemic rabbits. No significant changes in HDL-C levels were produced in all four groups.
Figure 6:
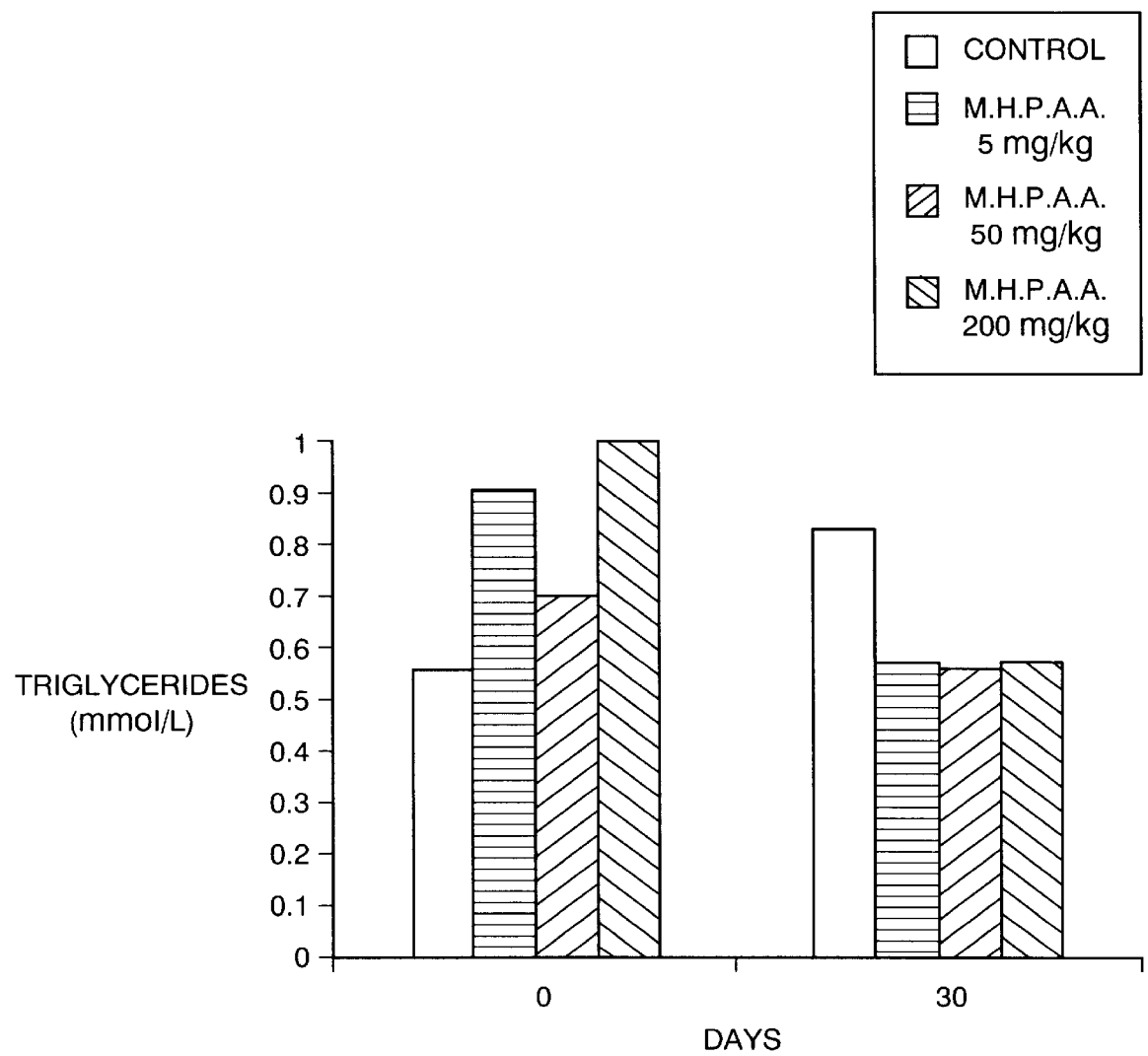
FIG. 6 illustrates the effect of M.H.P.A.A. on serum triglycerides and FIG. 7 on serum triglyceride changes in normocholesterolemic rabbits.
Figure 7:
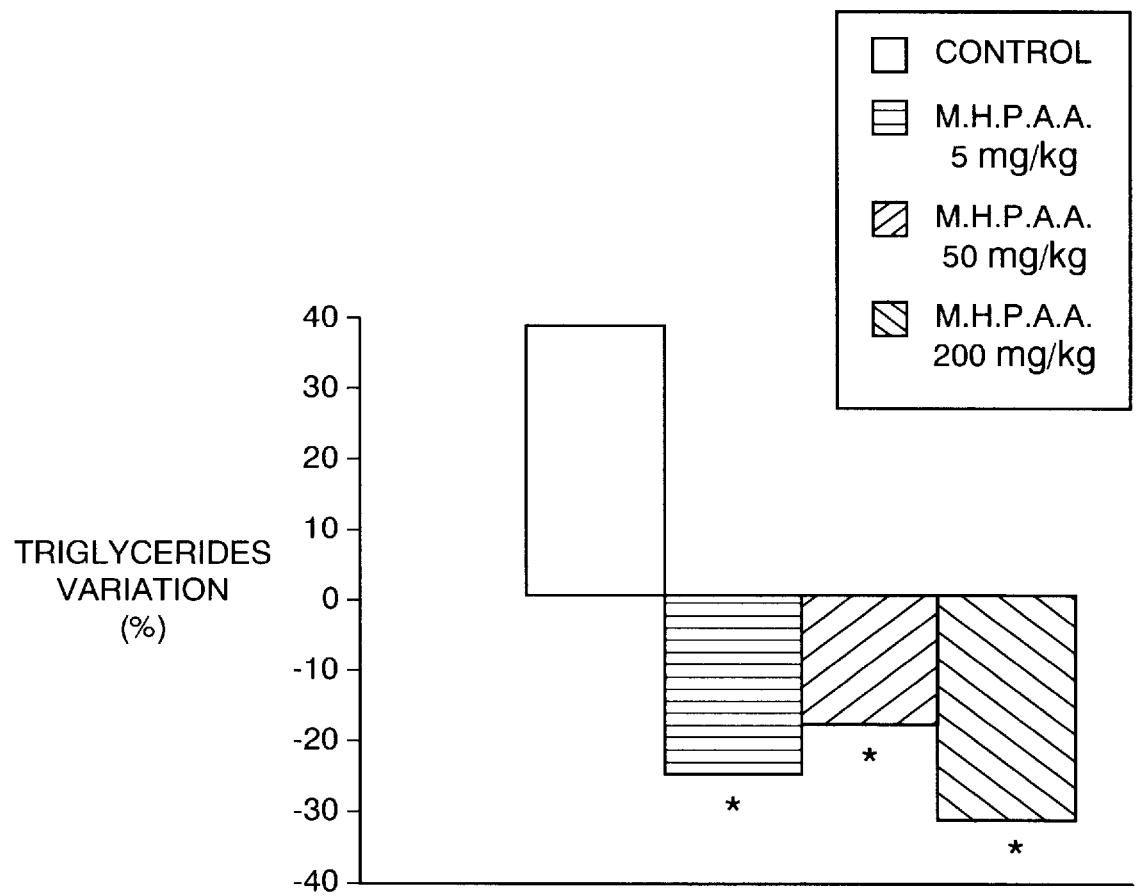

Comparison of triglycerides percent changes between treated and control groups were also significant (Mann Whitney U, *p<0.05), but no dose-effect relationship was observed.

EXAMPLE 11

Male New Zealand rabbits were distributed randomly in 4 groups: a control group (only receiving vehicle by gastric gavage) and 3 groups treated M.H.P.A.A., octacosanol and hexacosanol, repsectively at 5 mg/kg. Serum lipid profile was determined at baseline and 30 days before treatment. M.H.P.A.A. decreased significantly total cholesterol and LDL-C. Moreover, levels of cholesterol, LDL-C and triglycerides of M.H.P.A.A.-treated rabbits were significantly lower than those of the controls. Nevertheless, the changes on serum lipid profile occurred in groups treated with octacosanol or hexacosanol did not achieve statistical significance as is shown in Table 13.

TABLE 13

Effects of M.H.P.A.A., octacosanol and hexacosanol on serum lipid profile (mmol/L) of New Zealand normocholesterolemic rabbits (mean values).

| Group | Dose (mg/kg) | Baseline | After treatment |
|---|---|---|---|
| Total cholesterol | | | |
| Controls | 0 | 2.5 | 2.3 |
| M.H.P.A.A. | 5 | 2.8 | 1.6*+ |
| Octacosanol | 5 | 2.7 | 2.2 |
| Hexacosanol | 5 | 2.6 | 2.4 |
| LDL-C | | | |
| Control | 0 | 1.5 | 1.2 |
| M.H.P.A.A. | 5 | 1.3 | 0.6*+ |
| Octacosanol | 5 | 1.4 | 0.9 |
| Hexacosanol | 5 | 1.5 | 1.0 |
| Triglycerides | | | |
| Control | 0 | 0.80 | 0.82 |
| M.H.P.A.A. | 5 | 0.78 | 0.55* |
| Octacosanol | 5 | 0.77 | 0.70 |
| Hexacosanol | 5 | 0.80 | 0.78 |

*$p < 0.05$ comparison with controls (Mann Whitney U test)
+$p < 0.05$ comparison with baseline (Wilcoxon)

EXAMPLE 12

After 5 weeks of diet-only period, forty five outpatients whom cholesterol and LDL-C values were not enough controlled by diet received tablets containing 5 mg of M.H.P.A.A. (twice-a-day at lunch and dinner) or placebo for 6 weeks. During this active treatment period, dietary conditions were mantained. Lipid profile levels were determined at baseline (end of the diet-only period) as well as 4 and 6 weeks after therapy. M.H.P.A.A. reduced significantly total serum cholesterol by 16.23% and LDL-C by 21.33%. Also cholesterol to HDL-C and LDL-C to HDL-C ratios were significantly reduced to 17.67% and 22.28%, respectively (p<0.05 Wilcoxon test for paired data). In all patients levels of both total cholesterol and LDL-C were lower 6 weeks after treatment that at baseline. Changes on other lipid profile fractions were non significant, results are shown in Tables 14 and 15.

TABLE 14

Effects of M.H.P.A.A. (10 mg/day, 5 mg twice-a-day) on serum lipid profile (mmol/L) in patients with Type II hyperliproteinemia

| | n | Baseline (X + SD) | week 6 (X + SD) |
|---|---|---|---|
| Total cholesterol | | | |
| M.H.P.A.A. | 22 | 7.43 + 1.29 | 6.21 + 1.38***"" |
| placebo | 23 | 6.97 + 0.72 | 6.70 + 0.75* |
| LDL-C | | | |
| M.H.P.A.A. | 22 | 5.54 + 1.22 | 4.35 + 1.31***""a |
| placebo | 23 | 5.07 + 0.63 | 4.97 + 0.67 |
| HDL-C | | | |
| M.H.P.A.A. | 22 | 1.03 + 0.26 | 1.10 + 0.28 |
| placebo | 23 | 1.13 + 0.31 | 1.02 + 0.28 |
| Triglycerides | | | |
| M.H.P.A.A. | 22 | 2.41 + 0.94 | 1.74 + 0.88 |
| placebo | 23 | 2;03 + 0.64 | 1.87 + 0.67 |
| VLDL-C | | | |
| M.H.P.A.A. | 22 | 1.09 + 0.43 | 0.79 + 0.40 |
| placebo | 23 | 0.92 + 0.29 | 0.85 + 0.31 | n number of patients
*$p < 0.01$; ***$p < 0.0001$ comparison with baseiine (Wilcoxon)
a$p < 0.05$ comparison with placebo, absolute values, Mann Whitney U test
""$p < 0.001$ comparison with placebo (Mann Whitney U test)
"""$p < 0.00001$ comparison with placebo (Mann Whitney U test)

TABLE 15

Effects of M.H.P.A.A. (10 mg/day, 5 mg twice-a-day) on serum lipid ratios (mmol/L) in patients with Type II hyperliproteinemia

| | n | Baseline (X + SD) | week 6 (X + SD) |
|---|---|---|---|
| LDL-C to HDL-C | | | |
| M.H.P.A.A. | 22 | 5.71 + 1.82 | 4.18 + 1.59**""a |
| placebo | 23 | 4.92 + 1.85 | 5.30 + 1.79 |
| Cholesterol to HDL-C | | | |
| M.H.P.A.A. | 22 | 7.65 + 2.18 | 5.94 + 1.81*" |
| placebo | 23 | 6.69 + 2.21 | 7.06 + 2.05 |

*$p < 0.05$; ** $p < 0.01$ comparison with baseline (Wilcoxon)
a$p < 0.05$ comparison with placebo, absolute values, Mann Whitney U test
"$p < 0.05$ comparison with placebo (Mann Whitney U test)
""$p < 0.01$ comparison with placebo (Mann Whitney U test)

EXAMPLE 13

A group of patients with Type II hyperlipoproteinemia received tablets containing 15 mg of the formulation after 8 weeks of diet only period (baseline). Lipid profile was determined at baseline and 8 weeks after therapy. The main results are summarized in Table 16. Formulation with M.H.P.A.A. significantly reduced serum total cholesterol by 16.44% and LDL-C by 23.51%.

Figure 8:
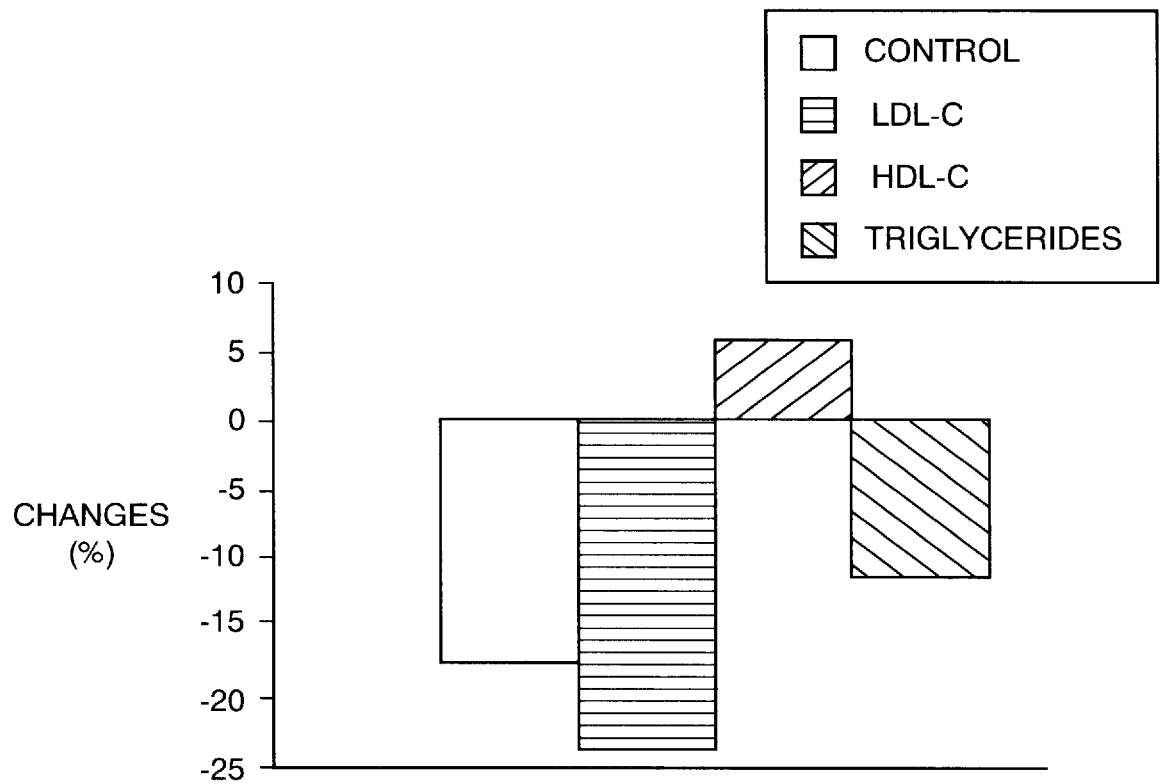

FIG. 8 shows the effects of M.H.P.A.A. on the lipid profile of patients with Type II hyperlipoproteinemia, whereby the changes of cholesterol, LDL-C and HDL-C are indicated as mean values and the change of triglycerides as median value. HDL-C raised 6.40%, while triglycerides and VLDL-C decreased 7.80% and 10.83%, respectively but these changes were not statistically significant. In Table 17 are shown the changes on the LDL-C to HDL-C and cholesterol to HDL-C ratios, they were decreased significantly by 29.07% and 23.72%, respectively.

TABLE 16

Effects of M.H.P.A.A. on serum lipids profile and lipoproteins in patients with Type II hyperliproteinemia

| Parameters | n | Baseline (X + SD) | n | 8 weeks (X + SD) |
|---|---|---|---|---|
| Cholesterol | 25 | 7.84 + 1.14 | 25 | 6.50 + 1.21**** |
| LDL-C | 17 | 5.86 + 1.11 | 18 | 4.33 + 1.32** |
| HDL-C | 19 | 1.03 + 0.44 | 20 | 1.21 + 0.46 |
| Triglycerides | 19 | 2.30 + 1.42 | 20 | 2.14 + 1.06 |
| VLDL-C | 19 | 1.05 + 0.64 | 20 | 0.97 + 0.48 | p < 0.01; **p < 0.0001 (Wilcoxon test)

TABLE 17

Effects of M.H.P.A.A. on LDL-C to HDL-C and cholesterol to HDL-C ratios in patients with Type II hyperliproteinemia

| Parameters | n | Baseline (X + SD) | n | 8 weeks (x + SD) |
|---|---|---|---|---|
| LDL-C to HDL-C | 17 | 6.34 + 2.79 | 18 | 3.82 + 1.55** |
| Cholesterol to HDL-C | 19 | 8.83 + 3.49 | 20 | 6.07 + 2.17** |

**p < 0.01 (Wilcoxon test)

EXAMPLE 14

Firstly, it was investigated the effect of M.H.P.A.A. and its effect on ADP and collagen-induced platelet aggregation in rats. A group of male Sprague-Dawley rats weighing 250 to 350 g were distributed randomly between 2 experimental groups. M.H.P.A.A. was administered orally as a suspension in a Acacia gum-water vehicle by gastric gavage for 4 weeks. The following groups were included: Control group (only receiving vehicle) and a M.H.P.A.A. (25 mg/kg) treated group. To conduct the platelet aggregation assay, rats were anaesthetized in an ether atmosphere. Abdomens were opened and blood (5 ml) was drawn from the vena cava and mixed with 3.8% sodium citrate (1 volume of citrate per 9 of blood). Platelet-rich plasma (PRP) was obtained by blood centrifugation. Platelet-poor plasma (PPP) was obtained by PRP aliquot centrifugation 330xg for 15 minutes. Platelet aggregation was induced by ADP and by collagen and measured with a Payton aggregometer as described (McGregor L., Morazain R. and Renaud S.; 1980; Effect of dietary linoleic acid on platelet functions in the rat; Thrombosis Res. 20, 499). The statistical comparison of results between treatment and control groups was carried out using the non parametric Mann-Whitney U Test. Rats treated with M.H.P.A.A. at 25 mg/kg for 4 weeks showed a significant inhibition of platelet aggregation ex vivo when submaximum ADP and collagen doses were administered.

Figure 9:
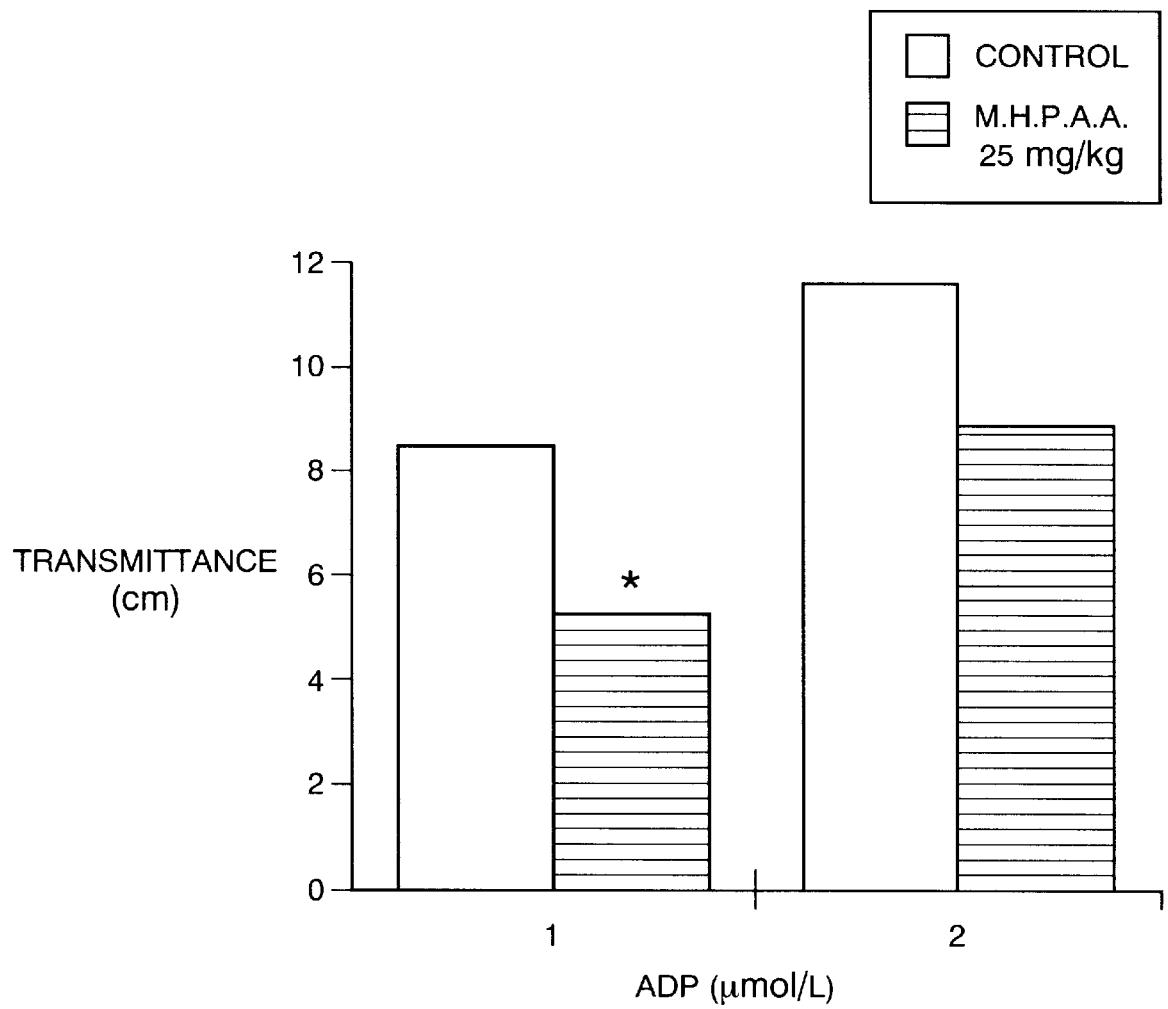
Figure 10:
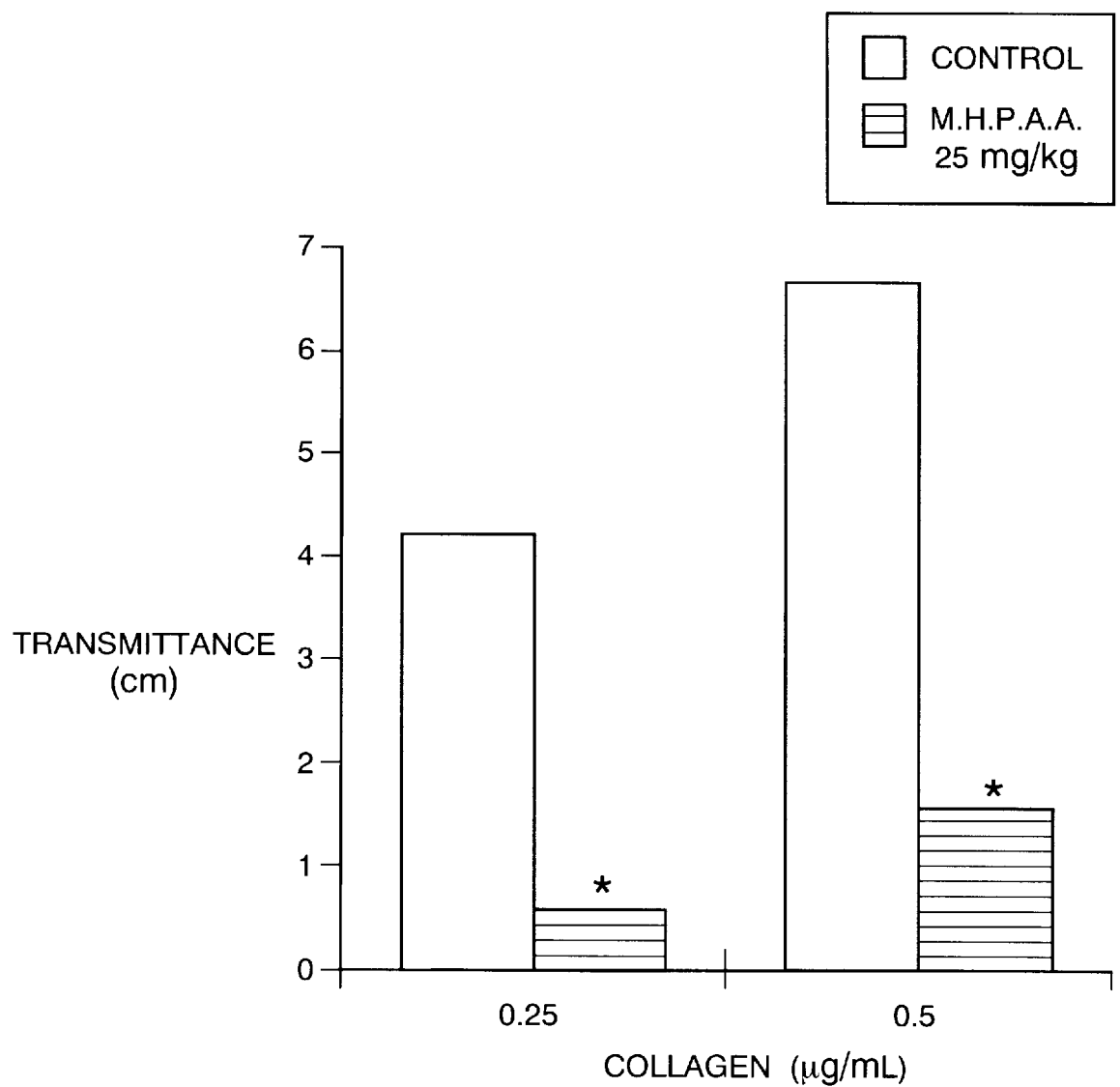

FIG. 9 shows ADP-induced platelet aggregation in rats administered with M.H.P.A.A. for 1 month and FIG. 10 the collagen-induced platelet aggregation in rats administered with M.H.P.A.A. for 1 month (*p <<0.05, Mann-Whitney U Tests; 15 cm 100% transmittance). M.H.P.A.A. administered orally for 4 weeks to the rats inhibited significantly ADP and collagen-induced platelet aggregation suggesting that M.H.P.A.A. acts as an antiplatelet drug.

EXAMPLE 15

Figure 11:
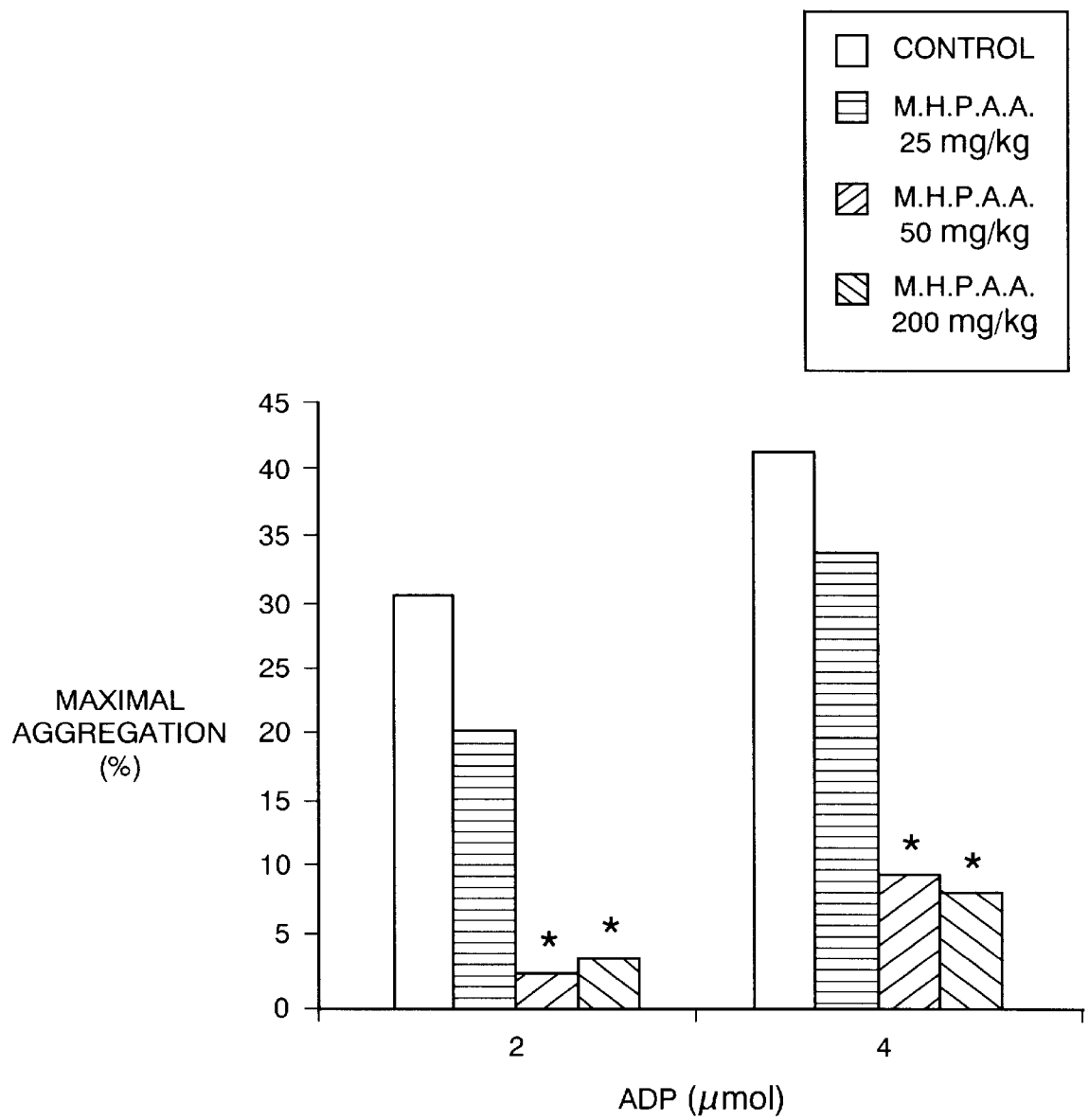
Figure 12:
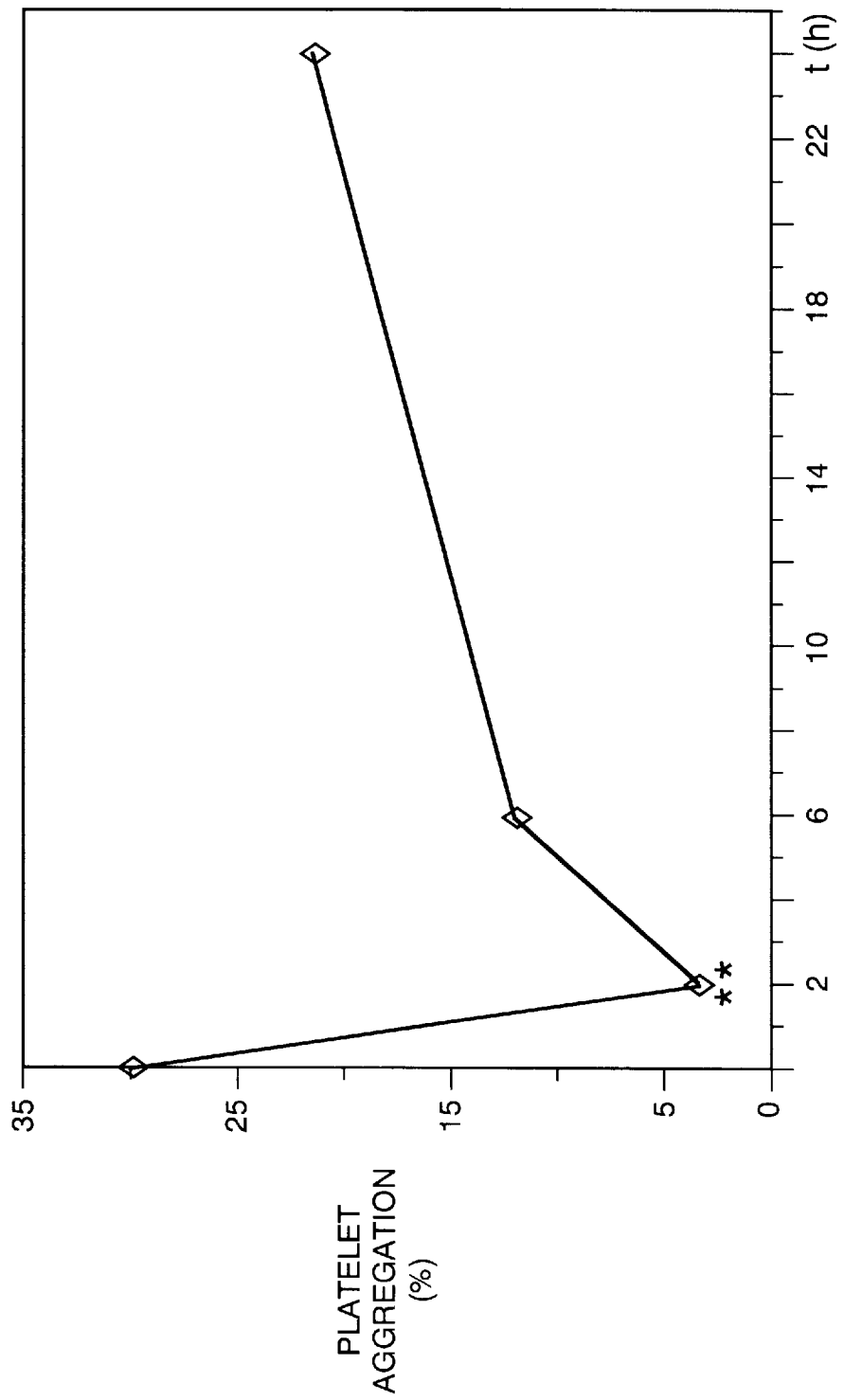

To characterize the effect of M.H.P.A.A. on ex vivo platelet aggregation in rats, some studies of the time course of its platelet antiaggregatory effects were done. For that purpose, Sprague-Dawley rats of both sexes weighing 250 to 350 g were distributed in 4 experimental groups: one control group and 3 groups treated with single doses of M.H.P.A.A. at 25, 50 and 200 mg/kg, respectively. Moreover, after 2, 6 and 24 hours of administering the 200 mg/kg dose, the effects on platelet agreggation were investigated. M.H.P.A.A. was prepared as described in Example 14 and administered orally as single doses, two hours prior to the experiment. Control animals receiving the same volume of vehicle. All animals were deprived of food, but had free access to water for 20 hours prior to the experiment. All animals were anaesthetized with ether and blood samples were drawn from vena cava and mixed with 3.8% sodium citrate (9 volumes of blood per 1 of anticoagulant). Blood was centrifuged at 250 g for 10 minutes to obtain platelet-rich plasma (PRP). Once PRP was isolated, the rest was centrifuged at 1300 g for 15 minutes to obtain platelet-poor plasma (PPP). Platelet aggregation was quantified by turbidimetric method (Born G., 1962; Aggregation of blood platelets by adenosine diphosphate and its reversal; Nature (London) 194, 927–929). Platelet aggregation levels were measured after calibrating the equipment at 0% of light transmission for PRP and at 100% for PPP. Aggregation curves were recorded for 5 minutes. FIG. 11 shows the effect of M.H.P.A.A. on ADP-induced platelet aggregation in rat platelet-rich plasma, *p<<0.05 (Mann Whitney U test). Results were expressed in percent of maximal aggregation (%). Groups were compared using the Mann-Whitney U test (p<<0.05). M.H.P.A.A. (50 and 200 mg/kg) administered 2 hours before blood sampling inhibited ADP-induced platelet aggregation, while lower doses (25 mg/kg) did not change significantly responses to ADP. The highest dose of M.H.P.A.A. (200 mg/kg) was chosen to study time course of anti-platelet effects. FIG. 12 shows the effect on ADP-induced platelet aggregation at a 2 $\mu$mol/L concentration, **p<<0.01. Although after 2 hours platelet aggregation was significantly inhibited, after 6 hours the inhibition was only marginally significant (p=0.06), while 24 hours after no statistical significance was obtained. Results show that oral administration of policosanol to rats two hours prior to blood sampling inhibited dose-dependently ADP-induced platelet agreggation in PRP of rats treated with M.H.P.A.A. at 50 and 200 mg/kg. The inhibitory effect of M.H.P.A.A. on ADP-induced aggregation is reversible, since 6 hours after treatment with it at 200 mg/kg, inhibition of platelet aggregation was only marginally significant, and 24 hours after treatment a lack of effectiveness was appreciated, showing that M.H.P.A.A. does not induce permanent cell modifications.

EXAMPLE 16

The effects of M.H.P.A.A. on "in vivo" intravascular platelet aggregation in rats and on collagen-induced mortality in mice were studied. Male Sprague Dawley rats weighing 250 to 300 g and 57BL6 female mice weighing 20 to 25 g were distributed randomly among different experimental groups. M.H.P.A.A. was prepared as described in Example 14, while ASA was dissolved in 5% NaHCO$_3$. Drugs were administered orally by gavage 2 hours before the assay. Animals received no food for 16 hours prior to oral administration of the drugs. Rats were given 1 ml/100 g body weight and mice 0.5 ml/20 g body weight, control animals received equivalent volumes of the vehicle. Four experimental groups were used in the study of the intravascular platelet aggregation in rats: 1) Controls, 2, 3 and 4 M.H.P.A.A. at 5, 10 and 20 mg/kg. Animals were anaesthetized i.p. with pentobarbital sodium (30–40 mg/kg). A cannula was inserted into a carotid artery for blood sampling before and 90 seconds after a 30 mg/kg collagen i.v. injection into the penile vein. Blood (900 µL) was collected in plastic tubes containing a 100 µL mixture with 0.7 mg/ml indomethacin and 19 mg/ml EDTA. An aliquote was used to determine platelet concentration in each sample through optic microscopic counting. Blood was then centrifuged and plasma malondialdehyde (MDA) concentration was quantified through the thiobarbituric acid method (Satoh M., 1978; Serum lipid peroxyde in cerebrovascular disorders determined by a new colorimetric method; Clin. Chim. Acta 90,34–43). Platelet count and plasma MDA concentration variations after injecting collagen were expressed as a percent of baseline values. Differences between control and treatment groups were determined using the Mann-Whitney U Test.

For the study of the collagen induced mortality in rats, the experimental groups were the following:

1) controls: animals only receiving the vehicle, but inducing mortality by a collagen intravenous injection;

2) Animals pretreated with M.H.P.A.A. at 360 mg/kg 2 hours prior collagen injection;

3) Animals pretreated with M.H.P.A.A. at 360 mg/kg 1, 4, 8 and 24 hours prior to mortality induction; and 4) Animals pretreated with M.H.P.A.A. at 180 mg/kg and ASA at 50 mg/kg 2 hours prior to the assay.

Acid-soluble veal skin collagen type III was prepared as described (Kimura Y., Kaube T. and Watanabe K., 1985; Effect of celostagel on platelet aggregation and experimental thrombosis; Arzneim Forsch Drug Res. 35, 114–1148) and used at final concentration of 2.5 mg/ml. A 0.1 ml/20 g injection was administrated via the retro-orbital plexus. This dose caused from 60 to 100% mortality in control animals. The comparison of the mortality percent between control and treatment animals was done using Fisher's Exact probability Test.

Figure 13:
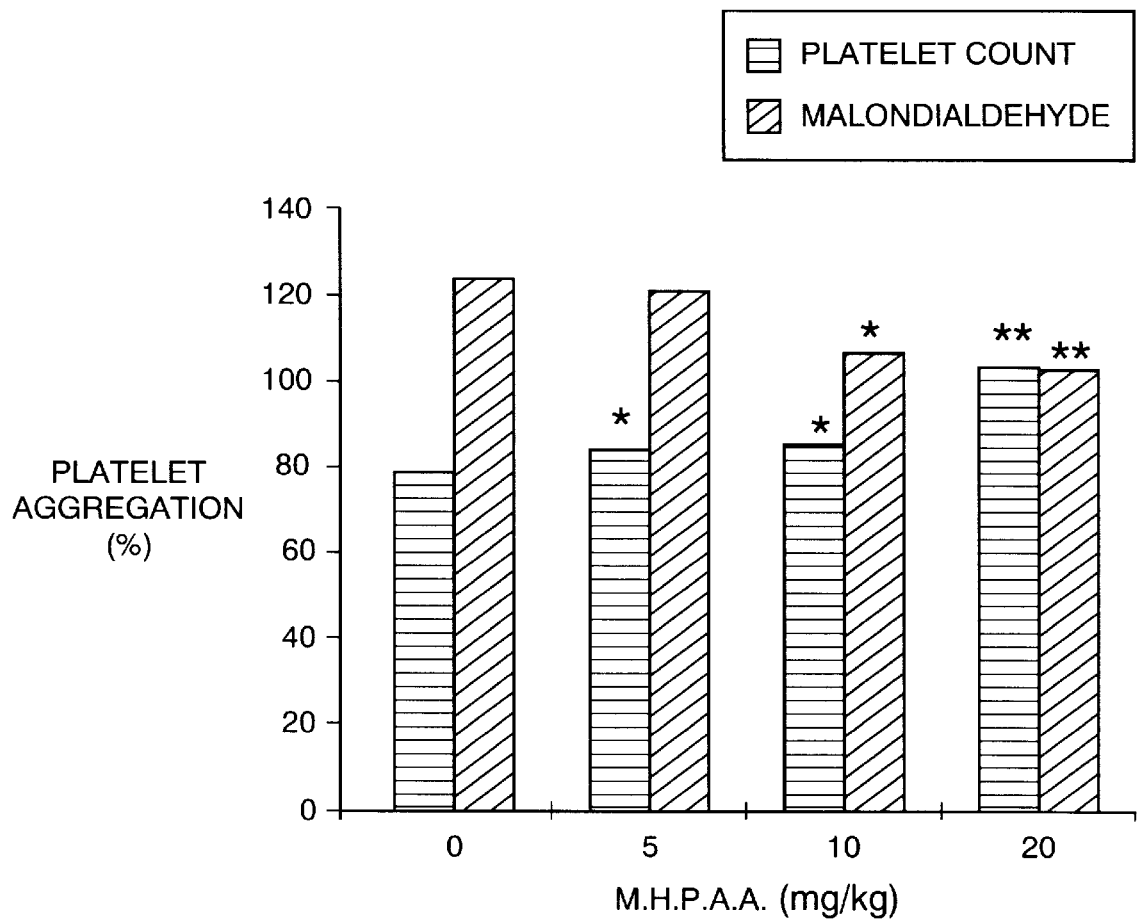

FIG. 13 shows the effect of M.H.P.A.A. on intravascular platelet aggregation in rats, *p<<0.05; **p<<0.01 (Mann-Whitney U Test). M.H.P.A.A. significantly inhibited the decrease in circulating platelet count and the simultaneous increase of MDA concentration in plasma induced by collagen.

Figure 14:
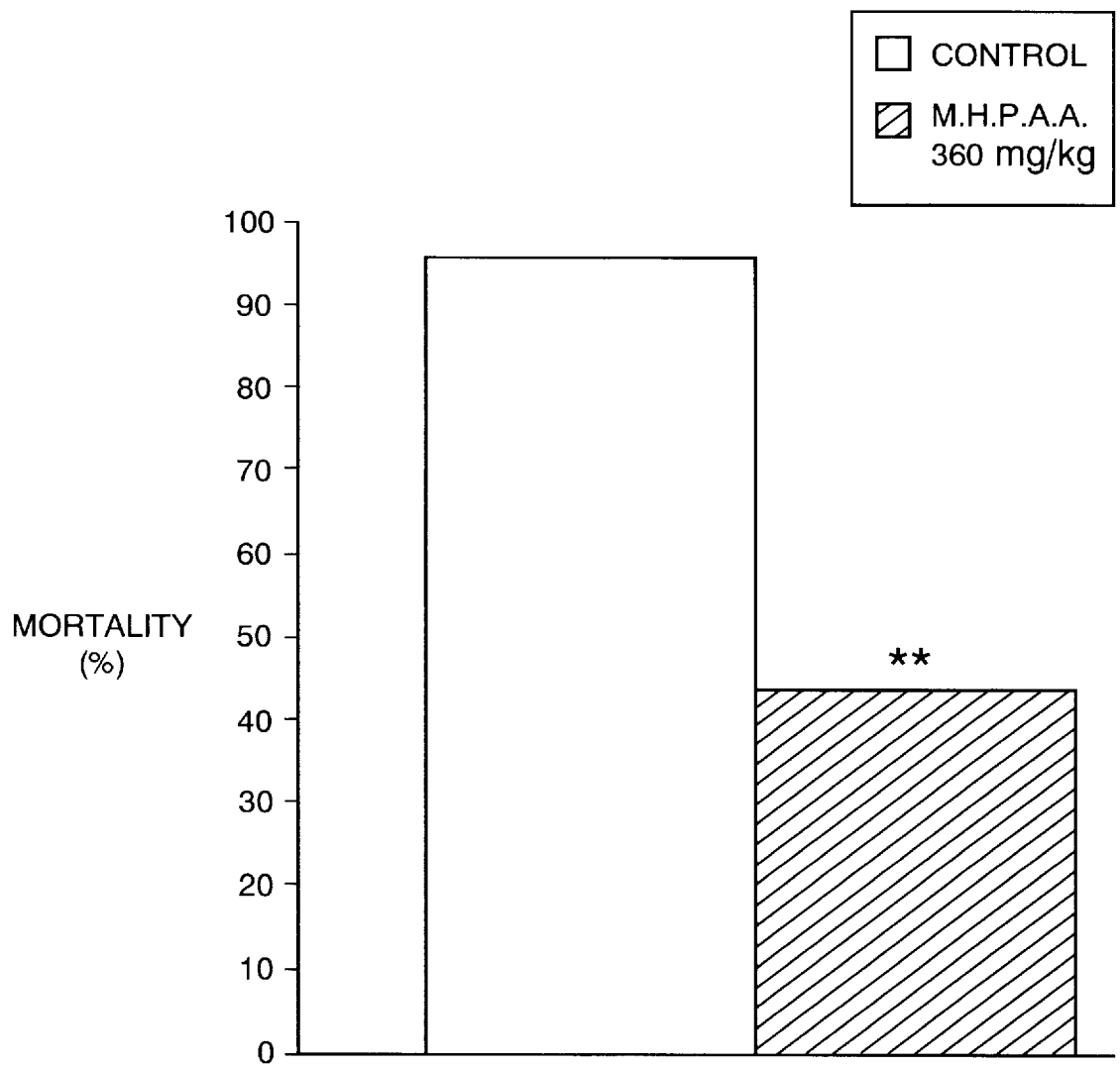
Figure 15:
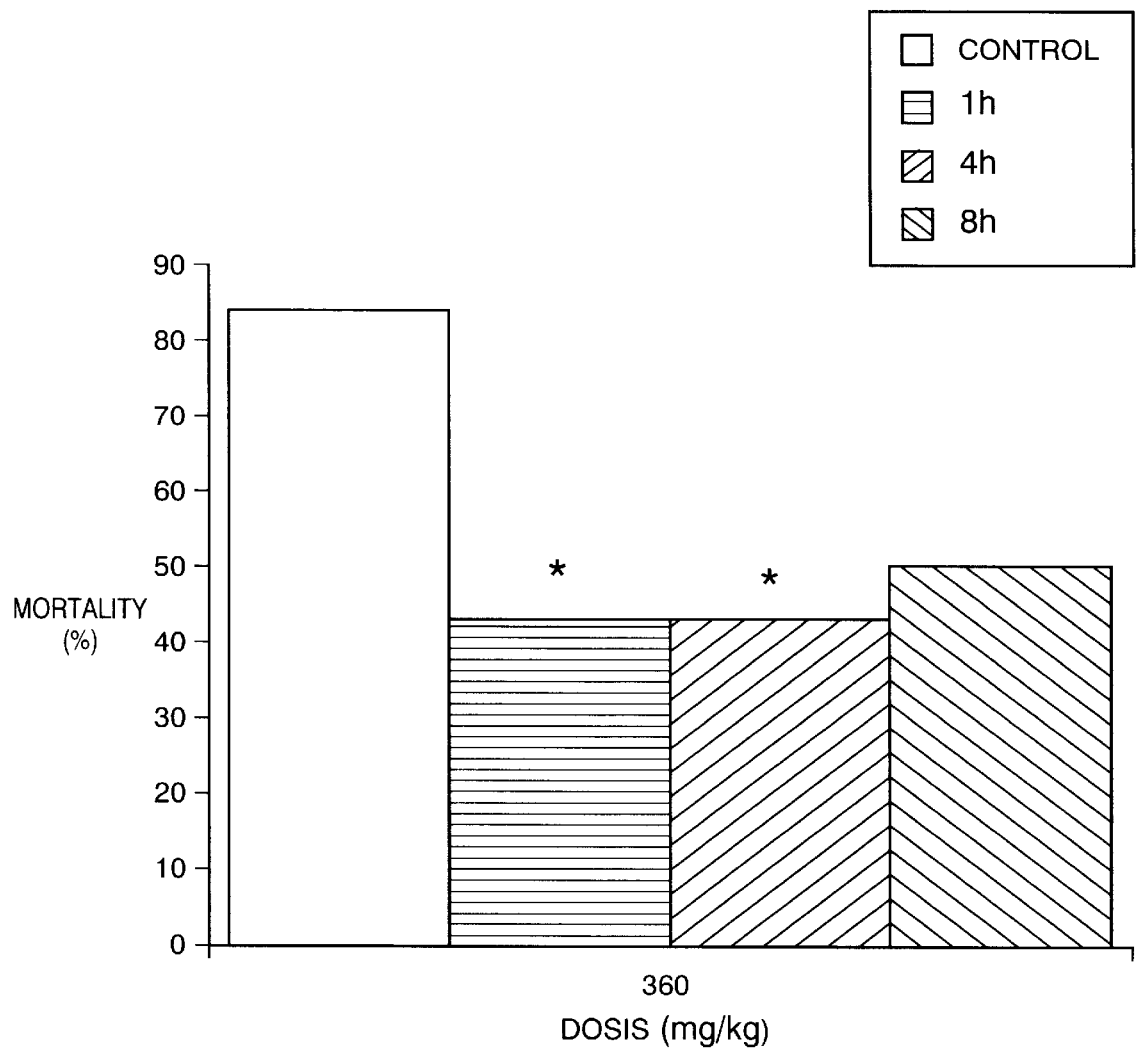

FIG. 14 demonstrates the effect of M.H.P.A.A. on collagen-induced mortality in C57BL6 mice, **p<<0.001 (Mann-Whitney U Test). Collagen-induced mortality was significantly reduced by M.H.P.A.A. at 360 mg/kg. This protective effect on the collagen induced mortality was observed when this dose was administered 1 and 4 hours prior to the assay, but significance was not obtained when administered 8 hours before the assay. FIG. 15 shows the effect of M.H.P.A.A. on collagen-induced mortality in C57BL6 mice, *p<<0.05 (Mann-Whitney U Test).

Figure 16:
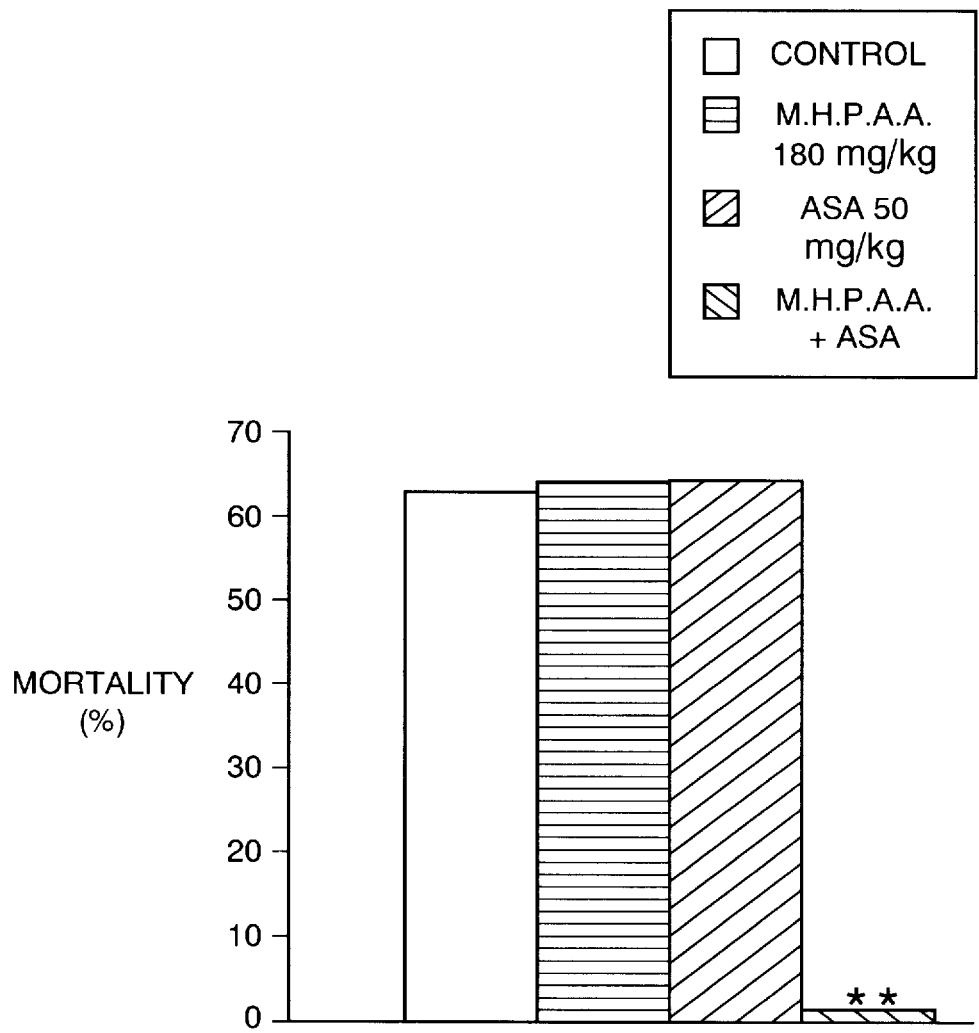

FIG. 16 illustrates the effect of combined administration of M.H.P.A.A. and ASA on collagen-induced mortality in mice, **p<<0.01 (Fisher's exact probability Test). The combination of M.H.P.A.A. (180 mg/kg) and ASA (50 mg/kg) also caused a significant statistical decrease in collagen-induced mortality, while both treatments proved uneffective when administered independently. Doses of M.H.P.A.A. and ASA that were uneffective when administered independently were obviously protective when administered together, thus indicating a synergism between M.H.P.A.A. and ASA antithrombotic effects.

EXAMPLE 17

For the analysis of M.H.P.A.A. effect on rat cerebral infarction, male Sprague Dawley rats weighing 290 to 330 g were distributed into the following experimental groups:

1) negative control: non-ligated rats receiving only the vehicle by gastric gavage;

2) positive control: ligated rats also receiving the vehicle by gastric gavage;

3) and 4) ligated rats receiving M.H.P.A.A. (5 and 25 mg/kg) by the same route.

The different treatments were administered daily for 4 weeks. The last one was administered 12 hours before ligation, as well as 8 and 24 hours after the ligation, as commonly used in this model.

For the induction of cerebral ischemia, animals were gently anaestethized and oligemia was produced by bilateral ligation of the common carotid arteries. Immediately after, sodium nitroprusside (0.8 mg/250 g) was injected subcutaneously to induce arterial hypotension. Carotid clamps were removed 60 minutes after and animals were observed for 72 hours and then sacrificed. Brains were rapidly removed and placed in an oven at 80° C. for 24 hours. Both wet and dry weight were estimated to determine the water content (edema) and the following formula was applied:

$$\text{Edema} = \frac{\text{Wet weight} - \text{dry weight}}{\text{Wet weight}} \cdot 100$$

The statistical analysis of the results was carried out using the non-parametric Mann-Whitney U test. M.H.P.A.A. at 25 mg/kg decreased significantly the cerebral edema ($p<<0.05$) when is administered daily for 4 weeks. This dose also reduced mortality rates and percent of animals with edema, though these other reductions did not reach significant levels. These findings show that M.H.P.A.A. at 25 mg/kg significantly protect cerebral ischemia experimentally induced in rats, since a significant reduction in the brain edema was produced. There was also a reduction in the percent of animals treated showing brain edema areas, but this reduction did not reach significant levels (Table 18).

TABLE 18

Effect of M.H.P.A.A. on rat-induced brain ischemia

| Group | Doses (mg/kg) | Edema | Percent of Mortality | Animals |
|---|---|---|---|---|
| (−) Control | 0 | 79.3 +/− 0.39 | — | — |
| (+) Control | 0 | 80.1 +/− 0.82 | 35 | 54.5 |
| M.H.P.A.A. | 5 | 80.0 +/− 0.91 | 40 | 33.3 |
| M.H.P.A.A. | 25 | 79.5 +/− 0.49* | 28 | 7.6 |

(−) controls: negative controls, (+) controls: positive controls;
*Significant differences compared with positive controls; p << 0.05 (Mann-Whitney U test)

EXAMPLE 18

To study the synergism between M.H.P.A.A. and aspirin on brain ischemia induced in rats, male Sprague Dawley rats weighing 250 to 300 g were distributed in 5 groups:

1) negative control (non ligated rats);

2) positive control (ligated animals receiving only the vehicle);

3) animals received orally by gavage 25 mg/kg of M.H.P.A.A.;

4) animals received orally ASA dissolved in 5% sodium bicarbonate 30 mg/kg;

5) rats administered orally ASA (30 mg/kg)+M.H.P.A.A. (25 mg/kg).

Figure 17:
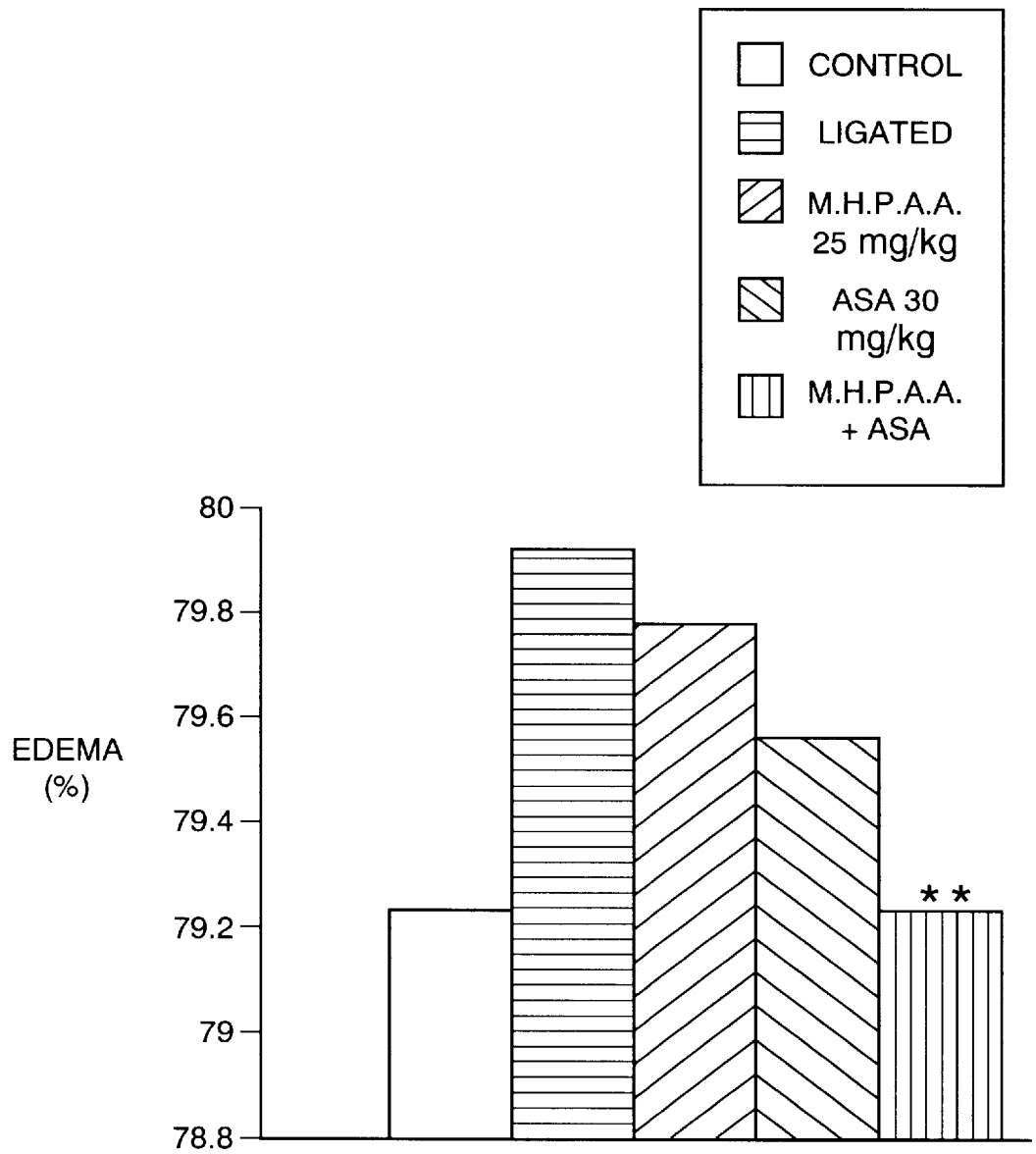

Treatments were administered 2 hours prior the experiment. For the ischemia induction, animals were gently anaesthetized with ether and common arteries were dissected and ligated. Hypotension was then induced by a subcutaneous injection of sodium nitroprusside (0.8 mg/250 g). Carotid clamps were removed 60 min after and animals were observed for 24 hours. They were sacrificed and brains were removed immediately and placed in an oven at 80° C. for 24 h to determine water content. Results were analyzed using the non parametric Mann-Whitney U test. FIG. 17 shows the synergism between M.H.P.A.A. and ASA in cerebral ischemia in rats; **$p<<0.01$ (Mann-Whitney U test). Neither M.H.P.A.A. nor aspirin reduced significantly brain ischemia when were separately administered to animals at the aforementioned doses. Nevertheless, when administered together a significant protection was obtained ($p<<0.01$). These results confirm a synergism between anti-ischemic effects of M.H.P.A.A. and ASA.

EXAMPLE 19

Mongolian gerbils of both sexes (60–80 g body weight) were used and adapted previously to laboratory conditions for a week. M.H.P.A.A. was administered by gastric gavage suspended in a Tween 20-water vehicle. Animals were distributed randomly into the following groups:

(1) positive control (ligated animals, only receiving the vehicle);

(2) M.H.P.A.A. (50 mg/kg) and (3) M.H.P.A.A. (300 mg/kg).

Figure 18:
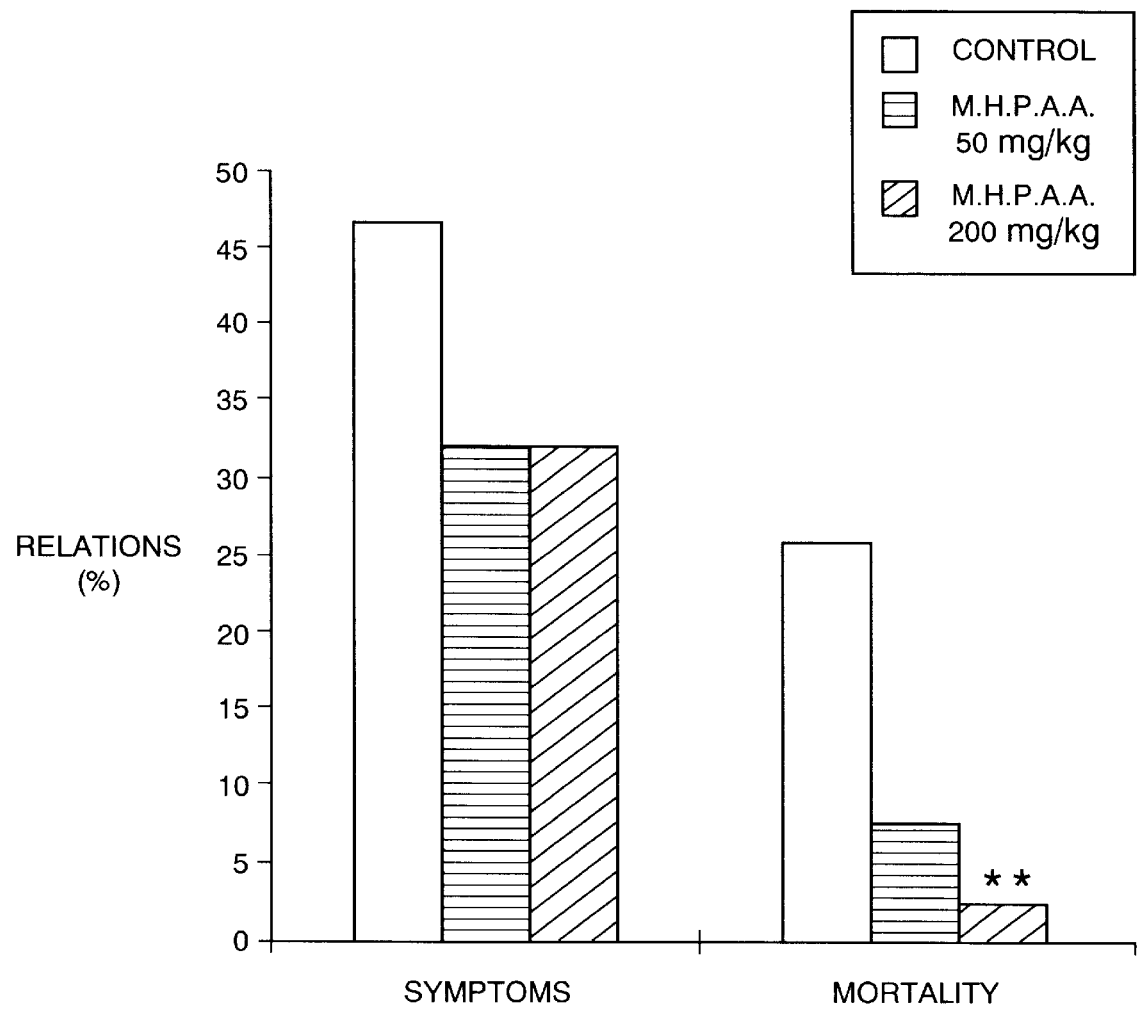

All treatments were administered two hours prior induction of brain ischemia. The left common carotid artery was exposed in the neck and double ligated with surgical thread under ether anaesthesia. The behavior of each animal was observed for 24 hours, recording the clinical symptoms of brain ischemia such as circling, rolling fits and seizures. Mortality was also recorded. Statistical comparison of the frequency of mortality and clinical symptons between groups were compared using the Fisher's Exact probability test. FIG. 18 shows the effect of M.H.P.A.A. on cerebral infarction induced in Mongolian gerbils; **$p<<0,05$ (Mann-Whitney U Test). Results show that treatment decreased symptoms and significantly reduced mortality.

It is well known that approximately 60% of Mongolian gerbils develop neurological deficits, such as circling behavior and rolling fits after ligation of common carotid artery. These symptoms have been associated with the fact that in approximately ⅔ of these animals there is an incompleteness or absence of connecting arteries between the basilar and carotid system. Moreover, almost a 80% of the animals showing clinical symptoms die within 72 hours after ligation.

Since the severity of cerebral infarction of all brain regions is difficult to assess, while mortality rate is easy to quantify, this parameter have been used commonly for evaluate putative anti-ischemic drugs. Our results show that M.H.P.A.A. (200 mg/kg) protects significantly the brain global ischemia induced by unilateral ligation of common artery in Mongolian gerbils. Thus, indicating usefulness of M.H.P.A.A. for preventing global ischemia development.

EXAMPLE 20

Effects of M.H.P.A.A. on gastric ulcer induced by different drugs were investigated. Sprague Dawley rats of both sexes, weighing 200 to 220 g were used. Animals were adapted to laboratory conditions for a week with water and food ad libitum. After a 24 hour fast, rats were divided ramdomly into two experimental groups. The first group was intraperitoneally injected M.H.P.A.A. at 25 mg/kg suspended in a Tween 20/water vehicle, while the second group (control) only received the same volume of vehicle. In each case, experimental procedure for induction of different types of drug-induced gastric ulcer was performed in both control and treated groups (two groups were used for each type of ulcer):

A) Gastric ulcer experimentally induced by C 4880 (Sigma). Procedure was simlar to that described by Awouters F., Nemegeens C. J. E. and Jansken P. A. J. (1985: A pharmacological analysis of the rat mast cell 5-HT gastric lesion test and the effect of ketanserin; Drug. Div. Res. 5, 303–312). For that, diphenhydramine was injected subcutaneously at 10 mg/kg and 30 minutes later C 4880 was injected endovenously. Animals were sacrificed 4 hours after C 4880 administration and stomachs were removed quickly, opened lengthwise the greater curvature and washed with distilled water. Then, mucosas were exposed and damaged area was measured by means of a magnifying glass. Results were expressed as percent of area showing damage. In this model, pretreatments (M.H.P.A.A. or vehicle) were administered 30 minutes before diphenhydramine injection.

B) Ulcer induced by alcohol. Procedure was performed as described by Zengil H., Onik E., Erean T. S. and Tarker R. K. (1987: Protective effect of ilopnost and UK 38485 against gastric mucosal damage by various stimuli; Prostaglandins Leukotrienes and Medicine 30, 61–67). For that, one hour after dosing M.H.P.A.A. or vehicle, rats were administered orally by gastric gavage ethanol 40% (1 ml/rat). Two hours later, rats were sacrificed and the procedure for quantifying gastric ulcer was performed as described.

Figure 19:
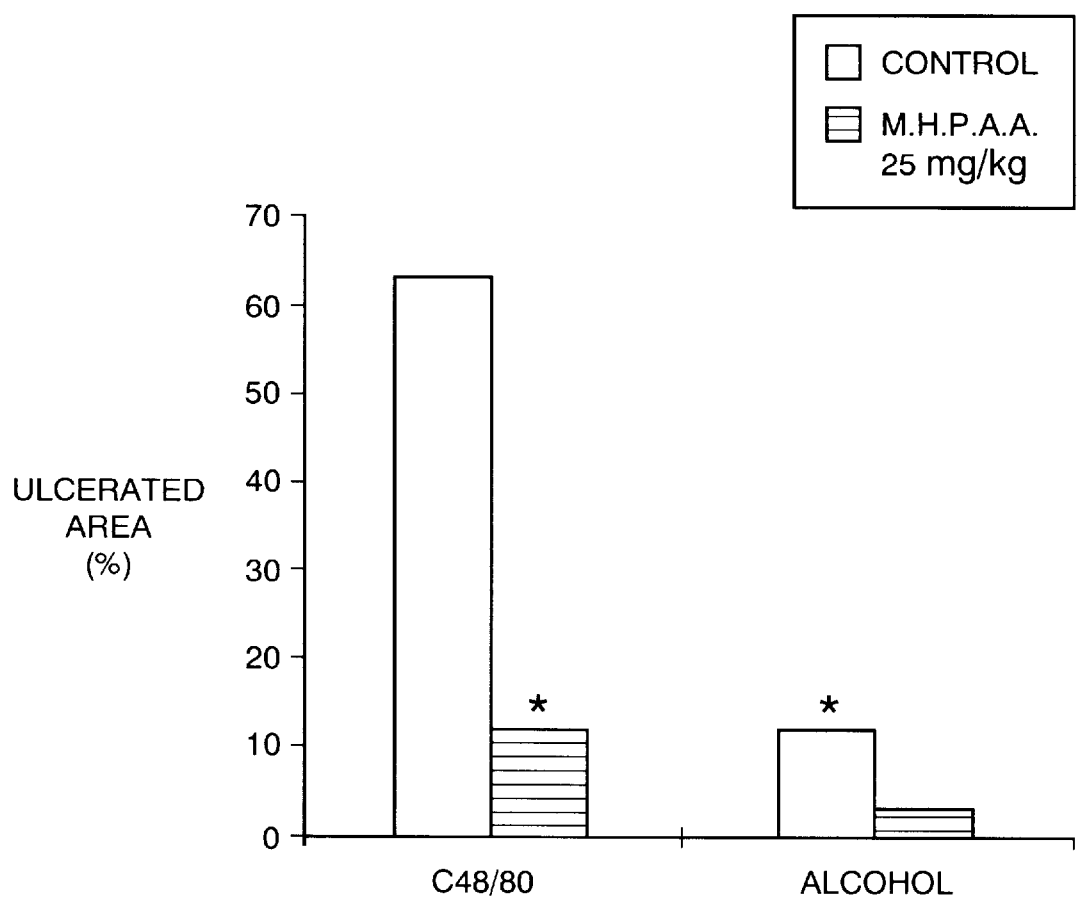

C) Gastric ulcer induced by ASA: Procedure was performed according to the same authors referred in the previous paragraph. One hour after treatment with M.H.P.A.A. or vehicle, rats were administered orally with ASA (100 mg/kg). Two hours later, rats were sacrificed and the procedure for gastric ulcer measurement was done as described. Comparisons between control and M.H.P.A.A.-treated groups were performed using the non parametric Mann-Whitney U test. FIG. 19 shows the effect of M.H.P.A.A. on C 4880 and alcohol-induced gastric ulcer; *$p<<0.05$. M.H.P.A.A. administered intraperitoneally (25 mg/kg) inhibited significantly the occurrence of gastric ulcer induced by C 4880, ethanol and ASA.

Moreover, as can be observed in Table 19, M.H.P.A.A. administered orally not only reduces $TxB_2$ but also increases $PgI_2$, thus very significantly reducing $TxB_2$ to $PgI_2$ ratio.

TABLE 19

Effect of M.H.P.A.A. and ASA on the $TxB_2$ levels and 6 keto PgF1a in mice serum.

| Control | $TxB_2$ (ng/ml) | 6 ketoPgF1a (ng/ml) | Index $TxB_2$/ KetoPgF1a |
|---|---|---|---|
| Control | 286 + 16.7 | 1.65 + 0.26 | 173 |
| ASA 50 mg/kg | 36.3 + 13.3**(a) | 1.12 + 0.41 | 46.5 |
| M.H.P.A.A. 180 mg/kg | 182 + 31.9**(b) | 3.91 + 0.4* | 32.4 |
| M.H.P.A.A. + AS | 9.25 + 5.4**(c) | 1.57 + 0.16 | 5.8 |

*$p < 0.05$; **$p < 0.01$; a = b = c (Mann Whitney U test)

The inhibition of the $TxB_2$ levels and the increase of $PgI_2$ induced by M.H.P.A.A. could explain the protective effect of the mixture against gastric ulcer. Thus, it is observed a highly significant decrease of the $TxB_2$ to $PgI_2$ ratio when combined treatment of M.H.P.A.A. and ASA is used. Moreover, this mechanism also could support alcohols mixture effects on the other drug-induced gastric ulcer.

EXAMPLE 21

Forty five outpatients from both sexes, aged from 25 to 70 years, with Type II hyperlipoproteinemia received, under double blind conditions, M.H.P.A.A. or placebo tablets once a day for 6 weeks (treated patients received M.H.P.A.A. at 5 mg/day). Before and after treatment the following parameters were investigated: bleeding time, platelet count, prothrombine time, antithrombin III activity, lysis time, plasmatic euglobulin fraction, platelet aggregation induced by ADP and malondialdehyde (MDA) concentration.

Table 20 summarizes the data. They show that none of the parameters related with the coagulation process were affected, while a significant difference between group of platelet agreggation-ADP induced was obtained. In addition, a marginally significant reduction of MDA was also observed (p=0.058).

TABLE 20

Effects of M.H.P.A.A. treatment in blood coagulation and platelet aggregation in patients with Type II hyperlipoproteinemia

| | time of analysis | Placebo | M.H.P.A.A. (5 mg/day) |
|---|---|---|---|
| Bleeding time | 0 | 2'47" +/- 1'26" | 2'31" +/- 1'24" |
| | 6 w | 2'10" +/- 1'34" | 2'08" +/- 1'06" |
| Platelet count | 0 | 201.23 +/- 29.98 | 198.13 +/- 39.48 |
| | 6 w | 188.55 +/- 35.99 | 175.33 +/- 40.87 |
| Prothrombine time | 0 | 13.67 +/- 1.80 | 14.43 +/- 4.18 |
| | 6 w | 13.40 +/- 1.10 | 13.69 +/- 2.25 |
| Fibrinogen | 0 | 2.64 +/- 0.46 | 2.84 +/- 0.54 |
| | 6 w | 2.81 +/- 0.52 | 2.92 +/- 0.44 |
| Antithrombin III activity | 0 | 79.95 +/- 7.50 | 82.86 +/- 11.97 |
| | 6 w | 91.78 +/- 9.69 | 93.67 +/- 14.62 |
| Lysis time | 0 | 247.27 +/- 30.10 | 230.43 +/- 48.19 |
| | 6 w | 248.64 +/- 55.72 | 228.48 +/- 45.39 |
| P.E.F. | 0 | 35.79 +/- 18.18 | 36.93 +/- 20.93 |
| | 6 w | 47.59 +/- 21.29 | 30.98 +/- 24.19 |
| ADP | 0 | 48.98 +/- 16.28 | 52.27 +/- 24.26 |
| | 6 w | 56.97 +/- 24.77 | 27.45 +/- 24.81 ++ |
| MDA | 0 | 2.99 +/- 1.75 | 2.45 +/- 2.31 a |
| | 6 w | 2.79 +/- 1.28 | 1.76 +/- 1.67 | a p = 0.058
+ p < 0.05
++ p < 0.01 (Mann Whitney U test)

EXAMPLE 22

M.H.P.A.A. administered orally or intraperitoneally increased significantly male rat sexual behavior. Thus, male rats were randomly divided into 3 experimental groups and adapted to lab conditions for a week. Copulatory activity with receptive estrogenized female rats was assessed before treatment to ensure the randomization assignment of treatments. Once corroborated, rats received orally by gavage M.H.P.A.A. or vehicle for 10 weeks and after treatment copulatory activity was again recorded (Table 21).

TABLE 21

Effect of M.H.P.A.A. on male rat sexual behavior

| | Number of | | Percent of rats showing (mg/kg) | |
|---|---|---|---|---|
| Treatment | Mounts | Erections | Mounting | Erections |
| controls | 8 + 14 | 8 + 13 | 50 | 66 |
| M.H.P.A.A. 0.5 | 21 + 21* | 22 + 21* | 75 | 75 |
| M.H.P.A.A. 5.0 | 24 + 19* | 37 + 44*** | 83* | 92* |
| M.H.P.A.A. 50 | 23 + 11* | 23 + 10*** | 100* | 100* |

*p < 0.05; ***p < 0.001 (comparison between groups)

The table shows mean +SD of mounts and penile erections as well as percent of animals showing both behaviors. Comparison between groups of mean values were done using the Mann Whitney U test and comparison of frequency of occurrence of each behavior was performed using the Fisher's Exact Probability test.

Sexual activity was also recorded 6 weeks after withdrawal of treatment. No further significant differences between groups were found, thus supporting that enhancement of male sexual activity observed during the active treatment period was drug-related. Nevertheless, no rebound effects were observed. These results indicate that increases of sexual activity induced by M.H.P.A.A. are reversible after wash-out period.

EXAMPLE 23

The effects of M.H.P.A.A. on sexual behavior of male monkeys (*Macaca arctoides*) were studied. Animals were randomly distributed into the following groups: a control group and 2 treated orally with M.H.P.A.A. at 2.5 and 25 mg/kg, respectively. In Table 22 are listed the data.

TABLE 22

Effects of M.H.P.A.A. on sexual behavior ex-copula and serum testoterone levels of Macaca arctoides monkeys (X + SD).

| Treatment (mg/kg) | No. of erections | No. of masturbations | Testosterone levels (mMol/L) |
|---|---|---|---|
| Control | 2 + 1 | 2 + 1 | 19.25 + 6.98 |
| M.H.P.A.A. 2.5 | 12 + 10 | 10 + 9 | 22.00 + 2.44 |
| M.H.P.A.A. 25 | 11 + 7 | 7 + 5 | 16.58 + 4.44 |

*p < 0.05 comparison with the control group (Mann Whytney U Test)

The results show that M.H.P.A.A. increased significantly the sexual activity ex-copula of captive male monkeys, since the number of penile erections and masturbations were increased significantly compared with controls. Nevertheless, no significant differences in serum levels of testosterone between treated animals and controls were found. This example suggests that the administration of the formulation increases sexual behavior in treated animals, and that this effect is not related to the level of masculine hormones found in the group of monkeys. No other component of the general behavior of monkeys was affected. It indicates that probably the stimulating effects of M.H.P.A.A. are mainly exerted not on the central nervous system, but on peripheral effectors. Taking into account effects of M.H.P.A.A. of $TxA_2$ to $PgI_2$ ratio, stimulation of nitric oxide (NO) release on corpora cavernosa cannot be discarded as the mechanism responsible of this action.

EXAMPLE 24

As described, M.H.P.A.A. stimulates sexual behavior in male rats. Since octacosanol is the main component of M.H.P.A.A., a comparison between the effects of octacosanol and M.H.P.A.A. alone on male rats sexual behavior was done. Male and female Wistar rats were adapted for a week to lab conditions. Females were ovariectomized at least 2 weeks prior use. For experiments, they were injected subcutaneously with 0.5 mg/kg estradiol benzoate 50–80 hours prior to mating test and with progesterone 5–8 hours before. M.H.P.A.A. was suspended in a Tween 20/water vehicle and injected intraperitoneally for 3 weeks. Octacosanol was similarly prepared and administered. Controls animals only received vehicle.

Animals were distributed randomly into 3 groups: 1) controls, 2) M.H.P.A.A. (1.54 mg/kg) and 3) octacosanol (1 mg/kg). Taking into account the relative concentration of octacosanol into the mixture, the abovementioned doses guarantee the same dosage of octacosanol on both treated groups. Copulatory activity was observed at baseline (to ensure an adequate randomization of the sexual activity in each group) and 3 weeks after treatment. Penile erections and mounts stimulated by receptive females were recorded for 90 minutes. Comparison between groups were done using the Mann Whitney U test. At baseline, sexual activity was similar in all groups, but 3 weeks after treatment, the number of erections and mounts in both treated groups were significantly higher than those of controls. On the other hand, mounts and erections were significantly higher in the M.H.P.A.A. group than in the octacosanol group (Table 23).

These results agree with previous results showing effects of the alcohols mixture stimulating male rat sexual behavior, but also showing stimulating effects induced by octacosanol. Nevertheless, sexual behavior was significantly higher in the alcohols mixture treated than in the octacosanol group. It indicates that the stimulating effect of the alcohols mixture is related to the presence of octacosanol, but that the other alcohols present in the mixture positively modulate in some way the stimulating effect on sexual activity.

TABLE 23

Effects of M.H.P.A.A. and octacosal on male rats sexual behavior

| Treatment | X + SD | |
|---|---|---|
| | Mounts | Erections |
| Controls | 44 + 23 | 40 + 19 |
| M.H.P.A.A. | 175 + 87**" | 174 + 87**" |
| Octacosanol | 81 + 40* | 76 + 37 |

*$p < 0.05$; **$p < 0.001$ comparison with controls; "$p < 0.05$ comparison with octacosanol-group (Mann Whitney U test).

We claim:

1. A mixture of higher primary aliphatic alcohols from 24 to 34 carbon atoms comprising 1-tetracosanol, 1-hexacosanol, 1-heptacosanol, 1-octacosanol, 1-nonacosanol, 1-triacontanol, 1-dotriacontanol and 1-tetratriacontanol having the following quantitative composition:

| 1-tetracosanol | 0.5–1.0% |
|---|---|
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0%. |

2. The mixture of higher primary aliphatic alcohols according to claim 1, having by the following quantitative composition:

| 1-tetracosanol | 0.80 +/– 0.1% |
|---|---|
| 1-hexacosanol | 6.7 +/– 0.3% |
| 1-heptacosanol | 3.0 +/– 0.3% |
| 1-octacosanol | 65.6 +/– 3.4% |
| 1-nonacosanol | 0.7 +/– 0.1% |
| 1-triacontanol | 12.5 +/– 0.6% |
| 1-dotriacontanol | 5.0 +/– 0.4% |
| 1-tetratriacontanol | 0.8 +/– 0.1%. |

3. The mixture of higher primary aliphatic alcohols according to claim 1 characterized by a combination with acetyl salicylic acid in a quantitative ratio from 20:1 to 1:20 further comprising excipients selected from the group consisting of agglutinants, disintegrators, lubricants, sliders or fillers.

4. The mixture of higher primary aliphatic alcohols according to claim 2 further comprising acetyl salicylic acid in a quantitative ratio from 20:1 to 1:20 further comprising excipients selected from the group consisting of agglutinants, disintegrators, lubricants, sliders or fillers.

5. The mixture of higher primary aliphatic alcohols according to claim 3 further comprising acetyl salicylic acid in a quantitative ratio from 10:1 to 1:10.

6. The mixture of higher primary aliphatic alcohols according to claim 4 further comprising acetyl salicylic acid in a quantitative ratio from 10:1 to 1:10.

7. A pharmaceutical formulation comprising 0.5–15.0% weight of a mixture of alcohols constituted by the following quantitative composition:

| 1-tetracosanol | 0.5–1.0% |
|---|---|
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | and further comprising as pharmaceutical excipients, appropriate fillers, agglutinants, disintegrators, and lubricants.

8. The pharmaceutical formulation of claim 7 in the form of tablets, capsules or granules.

9. The pharmaceutical formulation according to claim 7 comprising 0.5–15.0% weight of a mixture of alcohols constituted by the following quantitative composition:

| 1-tetracosanol | 0.8 +/– 0.1% |
|---|---|
| 1-hexacosanol | 6.7 +/– 0.3% |
| 1-heptacosanol | 3.0 +/– 0.3% |
| 1-octacosanol | 65.6 +/– 3.4% |
| 1-nonacosanol | 0.7 +/– 0.1% |
| 1-triacontanol | 12.5 +/– 0.6% |

-continued

| | |
|---|---|
| 1-dotriacontanol | 5.0 +/- 0.4% |
| 1-tetratriacontanol | 0.8 +/- 0.1%. |

10. A pharmaceutical formulation comprising the mixture of higher primary aliphatic alcohols constituted by the following quantitative compositions:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | in combination with acetyl salicylic acid in a quantitative ratio from 20:1 to 1:20, and pharmaceutically acceptable excipients selected from the group consisting of lactose, corn starch, saccharose, magnesium stearate, microcrystalline cellulose, sodium croscarmelose gelatin, cellulose acetophthalate, titanium dioxide, talc, and polyethylene.

11. The pharmaceutical formulation of claim 10 in the form of tablets, capsules, microgranules, or granules.

12. The pharmaceutical formulation of claim 10 having acetyl salicylic acid in a quantitative ratio from 10:1 to 1:10.

13. A pharmaceutical formulation comprising a mixture of higher primary aliphatic alcohols constituted by the following quantitative composition:

| | |
|---|---|
| 1-tetracosanol | 0.8 +/- 0.1% |
| 1-hexacosanol | 6.7 +/- 0.3% |
| 1-heptacosanol | 3.0 +/- 0.3% |
| 1-octacosanol | 65.6 +/- 3.4% |
| 1-nonacosanol | 0.7 +/- 0.1% |
| 1-triacontanol | 12.5 +/- 0.6% |
| 1-dotriacontanol | 5.0 +/- 0.4% |
| 1-tetratriacontanol | 0.8 +/- 0.1% | further comprising acetyl salicylic acid in a quantitative ratio from 20:1 to 1:20, and pharmaceutically acceptable excipients selected from the group consisting of lactose, corn starch, saccharose, magnesium stearate, microcrystalline cellulose, sodium croscarmelose gelatin, cellulose acetophthalate, titanium dioxide, talc, and polyethylene.

14. The pharmaceutical formulation of claim 13 in the form of tablets, capsules, microgranules, or granules.

15. The pharmaceutical formulation of claim 13, having acetyl salicylic acid in a quantitative ratio from 10:1 to 1:10.

16. The pharmaceutical formulation of claim 7, wherein said appropriate fillers comprise lactose or corn starch, wherein said agglutinants comprise sucrose, talc or microcrystalline cellulose, wherein said disintegrants comprise gelatin or sodium crosscarmellose, and wherein said lubricants comprise talc or magnesium stearate.

17. A method of administering the pharmaceutical formulation of claim 7 to animals (including humans) comprising administering of a daily dosage of 1 to 100 mg of said mixture.

18. The method of claim 17 wherein said daily dosage is 5 to 20 mg.

19. The method of claim 17 wherein said administering is orally or parenterally.

20. A method for obtaining a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | comprising the steps of:
 melting sugar cane wax;
 saponifying said melted wax;
 extracting the higher primary aliphatic alcohols.

21. The method of claim 20 wherein said saponification comprises a homogeneous phase, using solutions of alkaline and alkaline earth hydroxides.

22. Method according claim 21 wherein said hydroxides are sodium, calcium or potassium hydroxides.

23. The method of claim 21 wherein said extracting is a solid-liquid extraction systems using as organic solvents hydrocarbons from 6 to 9 carbon atoms, ketones from 3 to 8 carbon atoms, alcohols from 1 to 5 carbon atoms, haloforms or aromatic compounds as well as mixtures thereof.

24. Method according claims 23 wherein said hydrocarbons are pentane, hexane, heptane or octane.

25. Method according to claim 23 wherein said ketones are acetone, pentanone, methyl ethyl ketone, methyl butyl ketone and/or 3-heptanone.

26. Method according to claim 23 wherein said alcohols are methanol, ethanol, n-propanol, 2-propanol, n-butanol, 2-butanol, n-pentanol and terbutanol.

27. The method of claim 20 further comprising recrystallizing said extracted higher primary aliphatic alcohols using as organic solvents hydrocarbons from 6 to 9 carbon atoms, ketones from 3 to 8 carbon atoms, alcohols from 1 to 5 carbon atoms, haloforms or aromatic compounds as well as mixtures thereof.

28. Method of claim 20 wherein said haloform is dichloromethane, 1,2-dichloroethane, chloroform, tricholoro-ethane, 1,2- dicholoropropane or 1,2,3-trichloropropane.

29. Method according to claim 20 wherein said melting temperature of the sugar cane wax is ranged between 90° to 150° C., the hydroxide concentration is in the range of 5 to 30%, the time range of the saponification step is from 30 minutes on and the time range for the extraction step is from 1 hour to 20 hours.

30. Method for obtaining a mixture of higher primary aliphatic alcohols with the following quantitative composition:

| | |
|---|---|
| 1-tetracosanol | 0.8 +/- 0.1% |
| 1-hexacosanol | 6.7 +/- 0.3% |
| 1-heptacosanol | 3.0 +/- 0.3% |
| 1-octacosanol | 65.6 +/- 3.4% |
| 1-nonacosanol | 0.7 +/- 0.1% |
| 1-triacontanol | 12.5 +/- 0.6% |
| 1-dotriacontanol | 5.0 +/- 0.4% |
| 1-tetratriacontanol | 0.8 +/- 0.1% | comprising the steps of:
 melting sugar cane wax;
 saponifying said melted wax;
 extracting the higher primary aliphatic alcohols.

31. The method of claim 30 wherein said saponifying is in a homogeneous phase, comprising solutions of alkaline and alkaline earth hydroxides.

32. Method according to claim 30 wherein said hydroxides are sodium, calcium or potassium hydroxides.

33. The method of claim 30 wherein said extracting is a solid-liquid extraction systems using as organic solvents hydrocarbons from 6 to 9 carbon atoms, ketones from 3 to 8 carbon atoms, alcohols from 1 to 5 carbon atoms, haloforms or aromatic compounds as well as mixtures thereof.

34. Method according claim 33 wherein said hydrocarbons are pentane, hexane, heptane or octane.

35. Method according to claim 33 wherein said ketones are acetone, pentanone, methyl ethyl ketone, methyl butyl ketone and/or 3-heptanone.

36. Method according to claim 33 wherein said alcohols are methanol, ethanol, n-propanol, 2-propanol, n-butanol, 2-butanol, n-pentanol or terbutanol.

37. The method of claim 30 further comprising recrystallizing said extracted higher primary aliphatic alcohols using as organic solvents hydrocarbons from 6 to 9 carbon atoms, ketones from 3 to 8 carbon atoms, alcohols from 1 to 5 carbon atoms, haloforms or aromatic compounds as well as mixtures thereof.

38. Method of claim 36 wherein said haloform is dichloromethane, 1,2-dichloroethane, chloroform, tricholoro-ethane, 1,2-dicholoropropane or 1,2,3-trichloropropane.

39. Method according to claim 30 wherein benzene, toluene, ethyl benzene, phenol or p-methyl toluene are used as aromatic solvent in the extraction step.

40. Method according to claim 30 wherein said melting temperature of the sugar cane wax is ranged between 90° to 150° C., the hydroxide concentration is in the range of 5 to 30%, the time range of the saponification step is from 30 minutes on and the time range for the extraction step is from 1 hour to 20 hours.

41. A method of using a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | further comprising excipients selected from the group consisting of agglutinants, disintegrators, lubricants, sliders or fillers as antiplatelet agent.

42. A method of using a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | further comprising excipients selected from the group consisting of agglutinants, disintegrators, lubricants, sliders or fillers as antithrombotic agent.

43. A method of using a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | further comprising excipients selected from the group consisting of agglutinants, disintegrators, lubricants, sliders or fillers as anti-ischemic agent.

44. A method of using a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | further comprising excipients selected from the group consisting of agglutinants, disintegrators, lubricants, sliders or fillers as protective and/or curative agent against gastric ulcer induced by drugs.

45. A method of using a mixture of higher primary aliphatic alcohols with the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | together with acetyl salicylic acid and further comprising excipients selected from the group consisting of agglutinants, disintegrators, lubricants, sliders or fillers as an antiplatelet, anti-ischemic or antithrombotic agent.

46. A method of using of the mixture of higher primary aliphatic alcohols according to claim 45 wherein said mixture further comprises acetyl salicylic acid in a quantitative ratio from 20:1 to 1:20.

47. A method of using of the mixture of higher primary aliphatic alcohols according to claim 46 wherein said mixture further comprises acetyl salicylic acid in a quantitative ratio from 10:1 to 1:10.

48. A method of using a mixture of higher primary aliphatic alcohols with the following quantitative composition:

| | |
|---|---|
| 1-tetracosanol | 0.8 +/– 0.1% |
| 1-hexacosanol | 6.7 +/– 0.3% |
| 1-heptacosanol | 3.0 +/– 0.3% |
| 1-octacosanol | 65.6 +/– 3.4% |
| 1-nonacosanol | 0.7 +/– 0.1% |

| | |
|---|---|
| 1-triacontanol | 12.5 +/− 0.6% |
| 1-dotriacontanol | 5.0 +/− 0.4% |
| 1-tetratriacontanol | 0.8 +/− 0.1% | together with acetyl salicylic acid and further comprising excipients selected from the group consisting of agglutinants, disintegrators, lubricants, sliders or fillers as antiplatelet, anti-ischemic or antithrombotic agent.

49. A method of using of the mixture of higher primary aliphatic alcohols according to claim 48 wherein said mixture further comprises acetyl salicylic acid in a quantitative ratio from 20:1 to 1:20.

50. A method of using of the mixture of higher primary aliphatic alcohols according to claim 49 wherein said mixture further comprises acetyl salicylic acid in a quantitative ratio from 10:1 to 1:10.

51. A mixture of higher primary aliphatic alcohols from 24 to 34 carbon atoms characterized by the following quantitative composition:

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | produced according to the method of claim 20.

52. The method of claim 29 wherein said hydroxide concentration is from 15 to 25% and said saponifying is from about 2 to about 5 hours.

* * * * *